US006852906B2

(12) United States Patent
Craig et al.

(10) Patent No.: US 6,852,906 B2
(45) Date of Patent: Feb. 8, 2005

(54) ASSAY FOR MEASURING ENZYME ACTIVITY IN VIVO

(75) Inventors: Roger Kingdon Craig, Smallwood (GB); Simon Green, Dundee (GB); John Colyer, Bardsey (GB)

(73) Assignee: Cyclacel, Ltd., Scotland (GB)

( * ) Notice: Subject to any disclaimer, the term of this patent is extended or adjusted under 35 U.S.C. 154(b) by 283 days.

(21) Appl. No.: 10/147,354

(22) Filed: May 16, 2002

(65) Prior Publication Data

US 2003/0079235 A1 Apr. 24, 2003

Related U.S. Application Data

(63) Continuation-in-part of application No. PCT/GB00/04348, filed on Nov. 15, 2000.

(30) Foreign Application Priority Data

Nov. 18, 1999 (GB) .............................. 9927331

(51) Int. Cl.[7] .................. G01N 31/00; A01K 67/00; A01K 67/033; A01H 1/00; C12N 15/82
(52) U.S. Cl. ............................. 800/3; 800/8; 800/22; 800/278; 800/288
(58) Field of Search .................. 800/3, 8, 22, 278, 800/288

(56) References Cited

FOREIGN PATENT DOCUMENTS

| EP | 0 949 269 | 10/1999 |
|----|-----------|---------|
| WO | WO 94/07474 A | 4/1994 |
| WO | WO 97/27876 A | 8/1997 |
| WO | WO 97/28261 | 8/1997 |
| WO | WO 98/30715 | 7/1998 |
| WO | WO 98/36081 A2 | 8/1998 |
| WO | WO 98/36081 A3 | 8/1998 |
| WO | WO 98/45434 A | 10/1998 |
| WO | WO 99/18856 | 4/1999 |

OTHER PUBLICATIONS

Morgenstern and Land (1990) Nucleic Acids Res. 18 : 3587–3596.
Cosset et al. (1995) J. Virol. 69: 7430–7436.
Coffin RS, et al. (1998) Gene Therapy 5: 718–722.
Inaba K, et al. (1992) J. Exp. Med. 175: 1157–1167.
Caux C, et al. (1992) Nature 360: 258–261.
Zhao et al. (1995) J. Immunol 155:3904–3911.
Wilson and Hemmati–Brivanlou (1997) Neuron 18: 699–710.
Hemmati–Brivanlou and Melton (1997) Cell 88: 13–17.
Valenzuela et al. (1995) J. Neurosci 15: 6077–6084.
Sasai et al. (1994) Cell 79: 779–790.
Shimizu et al (1999) J. Biol. Chem. 274(46): 32961–32969.
Iemura et al. (1998) PNAS 95: 9337–9342.
Duojia Pan et al (1997) Cell 90: 271–280.
Altman et al. (1996) Science 274: 94–96.
Vose et al. (1997) Eur. J. Immunol. 7:753–757.
Belldegrun et al. (1988) Cancer Research 48: 206–214.
Belldegrun et al. (1988) The Journal of Immunology 142(12): 4520–4526.
Dunbar et al. (1998) Current Biology 8:413–416.
Lamb et al. (1983) J. Exp. Med 157: 1434–1447.
Eddison et al. (2000) PNAS 97(22) 11692–11699.
Sallusto F and Lanzavecchia A (1994) J. Exp. Med. 179: 1109–1118.
Lee et al. (2000) Current Biology 10:931–934.
Linheng et al. (1998) Immunity 8:43–55.
Medzhitov et al. (1997) Nature 388:384–397.
Romero et al. (1998) J. Exp. Med. 188(9) 1641–1650.
Spiess et al. (1987) JNCI 79(5) 1067–1075.
Takahashi et al. (2000) Nature Genetics 25: 390–396.
Heim, Roger and Tsien, Roger Y., "Engineering green fluorescent protein for improved brightness, longer wavelengths and fluorescence resonance energy transfer", Current Biology, vol. 6, pp. 178–182, 1996, referred to as XP 000676582.
Mitra et al, "Fluorescence resonance energy transfer between blue–emitting and red–shift excitation derivatives of the green fluorescent protein", Gene, pp. 13–17, 1996, referred to as XP 002033688.
Htun et al., "Visualization of glucocorticoid receptor translocation and intranuclear organization in living cells with a green fluorescent protein chimera", Proc. Natl. Acad. Sci. USA, vol. 93, pp. 4845–4850, May 1996, referred to as XP 002029560.

*Primary Examiner*—Deborah Crouch
*Assistant Examiner*—Valarie Bertoglio
(74) *Attorney, Agent, or Firm*—Kathleen M. Williams; Palmer & Dodge, LLP

(57) ABSTRACT

A method is provided for measuring in vivo in a transgenic non-human multicellular organism the activity of a cellular enzyme, which organism is transgenic by virtue of comprising one or more nucleic acid constructs encoding a binding domain and a binding partner thereof wherein: (i) the binding domain and/or binding partner comprise a site subject to post-translational modification by the cellular enzyme; (ii) modification of the site by the enzyme affects the interaction between the binding domain and the binding partner; and (iii) the binding domain and the binding partner each comprise a detectable label such that when the binding domain and binding partner interact, a detectable physical characteristic of one or both of the labels is altered, which method comprises measuring the interaction between the binding domain and the binding partner by measuring changes in the physical characteristic in one or more cells of the transgenic organism. A transgenic non-human multicellular organism is also provided.

19 Claims, 1 Drawing Sheet

ASSAY FOR MEASURING ENZYME ACTIVITY IN VIVO

Figure 1:
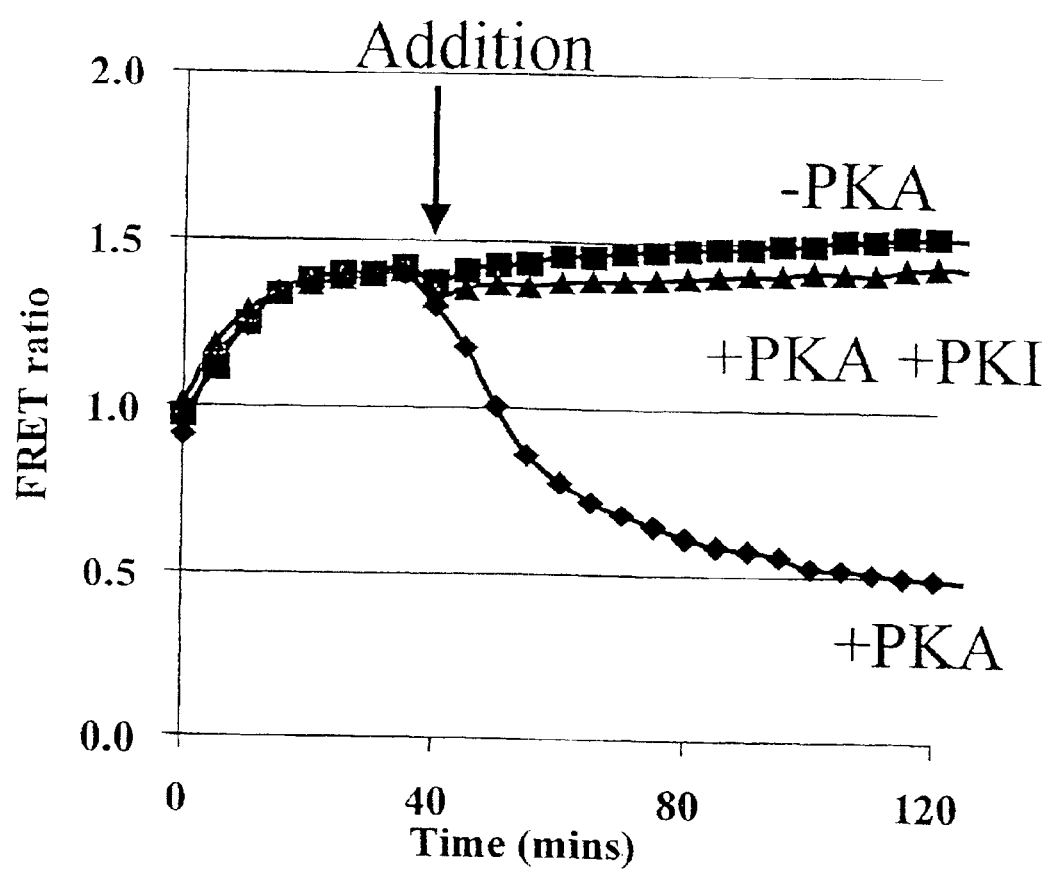

This application is a Continuation-in-part of PCT/GB00/04348, filed Nov. 15, 2000, designating the U.S., published May 25, 2001 as WO 01/36617 and claiming priority from GB 9927331.0 filed Nov. 18, 1999. All of the above-mentioned applications, as well as all documents cited herein and documents referenced or cited in documents cited herein, are hereby incorporated herein by reference.

FIELD OF THE INVENTION

The present invention relates to the use of detection procedures to measure the activity of a protein-modifying enzyme in vivo in a multicellular organism by monitoring the association of polypeptides that are modified by the enzyme, which polypeptides comprise a detectable label. The association of the polypeptides may be measured by techniques such as FRET, fluorescence correlation spectroscopy, fluorescence anisotropy or other techniques that indicate the proximity of two labeled polypeptide binding partners. Thus the labeled partners typically associate either in the presence or absence of a given post-translational modification to a site which is present in the binding domain and/or in the binding partner, but not in the detectable label, reflecting the modification state of one or both of the binding partners and, consequently, the level of activity of the protein-modifying enzyme.

SUMMARY OF THE INVENTION

There is a need in the art for an efficient means of monitoring enzyme activity in vivo, particularly continuously during real time to provide a dynamic assay system that also has the ability to resolve spatial information.

Accordingly the present invention provides a method of measuring in vivo in a transgenic non-human multicellular organism the activity of a cellular enzyme, which organism is transgenic by virtue of comprising one or more nucleic acid constructs encoding a binding domain and a binding partner thereof, wherein:

(i) the binding domain and/or binding partner comprise a site subject to post-translational modification by the cellular enzyme;
(ii) modification of the site by the enzyme affects the interaction between the binding domain and binding partner; and
(ii) the binding domain and binding partner each comprise a detectable label such that when the binding domain and binding partner interact, a detectable physical characteristic of one or both of the labels is altered, which method comprises measuring the interaction between the binding domain and the binding partner by measuring changes in said physical characteristic in one or more cells of the transgenic organism.

Preferably the binding domain and binding partner are present as separate nucleic acid constructs stably present in the germline of the transgenic organism.

Preferably said physical characteristic is light emission or absorption. More preferably said physical characteristic is the emission of fluorescent light. Preferably the detectable label is a fluorescent protein.

Preferably said enzyme is selected from a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, an NAD:Arginine ADP ribosyltransferase, a protease, a protein kinase and a protein phosphatase.

In a further embodiment, the method of the invention further comprises the step, prior to, during or after measurement of the physical characteristic, of contacting said one or more cells with a compound which modulates the activity of said enzyme.

The present invention further provides a method of identifying a compound capable of modulating the activity of a cellular enzyme which method comprises (i) contacting one or more cells of a transgenic non-human multicellular organism as defined in claim 1 with a candidate substance
(ii) measuring the activity of the enzyme in said cells by the method of claim 1; and
(iii) determining whether the activity of the enzyme is affected.

Compounds identified by the method of the invention as modulating in vivo, preferably inhibiting, the activity of the enzyme of interest, may be used in therapy. Accordingly the present invention also provides a compound identified by the method of the invention and a compound identified by the method of the invention for use in therapy.

The present invention further provides a transgenic non-human multicellular organism, which organism is transgenic by virtue of comprising one or more nucleic acid constructs encoding a binding domain and a binding partner, which constructs are stably present in the germline of the transgenic organism, wherein (i) the binding domain and/or binding partner comprise a site subject to post-translational modification by a cellular enzyme;
(ii) modification of the site by the enzyme affects the interaction between the binding domain and binding partner; and
(ii) the binding domain and binding partner each comprise a detectable label such that when the binding domain and binding partner interact, a detectable physical characteristic of one or both of the labels is altered.

Preferably the binding domain and binding partner are present as separate nucleic acid constructs stably present in the germline of the transgenic organism.

Preferably said physical characteristic is light emission or absorption. More preferably said physical characteristic is the emission of fluorescent light. Preferably the detectable label is a fluorescent protein.

Preferably said organism is an animal or a plant.

The present invention also provides a method of producing a transgenic organism of the invention which method comprises crossing a first transgenic organism comprising a nucleic acid construct encoding a binding domain comprising a detectable label, which construct is stably present in the germline of the first transgenic organism, with a second transgenic organism comprising a nucleic acid construct encoding a binding partner comprising a detectable label, which construct is stably present in the germline of the second transgenic organism.

In a further embodiment, the invention provides a method for monitoring activity of an enzyme in vivo which method comprises performing a detection step to detect dissociation of a binding domain from a binding partner therefor as a result of contacting one or both of said binding domain and said binding partner present in one or more cells of a transgenic organism of the invention with said enzyme, wherein said binding domain includes a site for post-translational modification and binds said binding partner in a manner dependent upon modification of said site and wherein detection of dissociation of said binding domain from said binding partner as a result of said contacting is indicative of enzyme activity.

Preferably said detection step is to detect a change in signal emission by said detectable label. Preferably said method further comprises exciting said detectable label and monitoring fluorescence emission.

In a preferred embodiment said method further comprises the step, prior to or after said detection step, of contacting said one or more cells with a compound which modulates the activity of said enzyme.

DETAILED DESCRIPTION OF THE INVENTION

Definitions

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference), chemical methods, pharmaceutical formulations and delivery and treatment of patients As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. The terms subunit and domain may also refer to polypeptides and peptides having biological function. A peptide useful in the invention will at least have a binding capability, i.e., with respect to binding as or to a binding partner, and also may have another biological function that is a biological function of a protein or domain from which the peptide sequence is derived. "Fragment thereof" typically refers to a selected region of the polypeptide that is of interest in a binding assay and for which a binding partner is known or determinable. "Fragment thereof" thus refers to an amino acid sequence that is a portion of a full-length polypeptide, between about 8 and about 1000 amino acids in length, preferably about 8 to about 300, more preferably about 8 to about 200 amino acids, and even more preferably about 10 to about 50 or 100 amino acids in length. "Peptide" refers to a short amino acid sequence that is 10 to 40 amino acids long, preferably 10 to 35 amino acids.

"Naturally-occurring" as used herein, as applied to a polypeptide or potynucleotide, refers to the fact that the polypeptide or polynucleotide can be found in nature. One such example is a polypeptide or polynucleotide sequence that is present in an organism (including a virus) that can be isolated from a source in nature.

As used herein, the terms "protein", "subunit" and "domain" refer to a linear sequence of amino acids which exhibits biological function. This linear sequence includes full-length amino acid sequences (e.g. those encoded by a full-length gene or polynucleotide), or a portion or fragment thereof, provided that portion or fragment maintains the biological function. The terms "subunit" and "domain" also may refer to polypeptides and peptides having biological function. A peptide useful in the invention will at least have a binding capability, i.e., with respect to binding as or to a binding partner, and also may have another biological function that is a biological function of a protein or domain from which the peptide sequence is derived.

"Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

The term "multicellular organism" here denotes all multicellular plants, fungi and animals except humans, i.e. prokaryotes and unicellular eukaryotes are excluded specifically. The term also includes an individual organism in all stages of development, including embryonic and fetal stages. A "transgenic" multicellular organisms is any multicellular organism containing cells that bear genetic information received, directly or indirectly, by deliberate genetic manipulation at the subcellular level, such as by microinjection or infection with recombinant virus Preferably, the organism is transgenic by virtue of comprising at least a heterologous nucleotide sequence encoding a binding domain or binding partner as herein defined.

"Transgenic" in the present context does not encompass classical crossbreeding or in vitro fertilization, but rather denotes organisms in which one or more cells receive a recombinant DNA molecule. Transgenic organisms obtained by subsequent classical crossbreeding or in vitro fertilization of one or more transgenic organisms are included within the scope of the term "transgenic".

The term "germline transgenic organism" refers to a transgenic organism in which the genetic information has been taken up and incorporated into a germline cell, therefore conferring the ability to transfer the information to offspring. If such offspring, in fact, possess some or all of that information, then they, too, are transgenic multicellular organisms within the scope of the present invention.

The information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

A. Binding Domains and Binding Partners

The invention provides transgenic animals comprising reporter molecules and methods for measuring the interactions between the reporter molecules, said interactions being modulated by the activity of protein modifying enzymes. These reporter molecules are typically naturally-occurring polypeptides which include natural binding domains, natural binding sequences and natural binding polypeptides, each as defined above, which are used in assays of the invention in combination with polypeptide binding partners, also as defined above. However, the use of derivatives or variants is also envisaged, for example to study the effect of mutations in the amino acid sequence on the function of the polypeptides.

By monitoring the association or dissociation of a binding domain, sequence or polypeptide and its binding partner in vivo, their activity can be measured in situ in a natural context. In particular, the effect of enzymes that modify the binding domain and/or binding partner can be studied. By way of an example, the transgenic organism of the invention may be administered a compound that affects a signal transduction pathway leading to modification of the binding domain and/or binding partner. The subsequent effect on binding may be observed in real time in situ, thus providing important pharmacokinetic and spatial information.

In such assays, one or both of the binding domain, sequence or polypeptide and its binding partner comprises a detectable label including, but not exclusively, a fluorescent or other light-emitting label, which is generally a polypeptide linked to the binding domain or binding partner. By measuring changes in signal emission during a physiological process, such as a response to a biologically active compound, the extent of association can be determined. Where this association is dependent on a post-translational modification, the activity of the cellular enzyme responsible for the modification can also be determined. An important feature of the invention is that such measurements (e.g., of a shift in FRET or other signal emitted by a detectable label) can be performed in real-time. This allows for sensitive assessment of reaction kinetics based upon the rate of change of the protein-binding-dependent signal emission or absorption by the label(s).

As used herein, the term "binding domain" in a three-dimensional sense refers to the amino acid residues of a first polypeptide required for modification-dependent binding between the first polypeptide and its binding partner. The amino acids of a "binding domain" may be either contiguous or non-contiguous and may form a binding pocket for modification-dependent binding. A binding domain typically includes at least 6 or more, preferably 10 or more, amino acids which are contiguous or non-contiguous, but are necessary for modification-dependent binding to the binding partner, and may include a full-length protein.

A binding domain which is of use in the invention is typically a "natural binding domain", i.e. a binding domain that exists in nature. In particular, the binding domain preferably exhibits modification-dependent binding to a binding partner in nature. A binding domain of use in the invention may be used as a discrete polypeptide domain or may be present in the context of a larger polypeptide molecule (i.e., one which comprises amino acids other than those of the natural binding domain) such as in its natural polypeptide context.

As used herein with regard to modification of a polypeptide, the terms "site" and "site sufficient for the addition of" refer to an amino acid sequence which is recognized by (i.e., a signal for) a modifying enzyme for the purpose of post-translational modification (i.e., addition or removal of a "moiety" as defined below) of the polypeptide or a portion thereof. A "site" additionally refers to the single amino acid which is modified. It is contemplated that a site comprises a small number of amino acids, as few as one but typically from 2 to 10, less often up to 30 amino acids, and further that a site comprises fewer than the total number of amino acids present in the polypeptide.

A "site", for post-translational modification may be present on either or both of a natural binding domain and its binding partner. If such sites are present on both the natural binding domain and the binding partner, binding between the natural binding domain and its binding partner may be dependent upon the modification state of either one or both sites. If a single polypeptide chain comprises the natural binding domain and its binding partner (or two natural binding domains), the state of post-translational modification of one or both sites will determine whether binding between the two domains occurs.

As used herein, the term "modification" or "post-translational modification" typically refers to the addition or removal of a chemical "moiety", as described herein, to/from a site on a polypeptide chain. However, proteolytic cleavage of the binding domain and or partner is also preferably included within the meaning of these terms. Often, the post-translational modification is reversible, such that repeating cycles of addition and removal of a modifying moiety may be observed.

As used interchangeably herein, the terms "moiety" and "group" refer to one of the post-translationally added or removed groups referred to herein: i.e., one of a ubiquitin moiety, a glycosyl moiety, a fatty acyl moiety, a sentrin moiety, an ADP-ribosyl or a phosphate moiety.

As used herein, the term "binding partner" refers to a polypeptide or fragment thereof (a peptide) that binds to a binding domain, sequence or polypeptide, as defined herein, preferably in a manner which is dependent upon the state of modification of a site for post-translational modification which is, at a minimum, present upon the binding domain, sequence or polypeptide; the binding partner itself may, optionally, comprise such a site and binding between the binding domain, fragment or polypeptide with its corresponding binding partner may, optionally, depend upon modification of that site. A binding partner does not necessarily have to contain a site for post-translational modification if such a site is not required to be present on it for modification-dependent association between it and a binding domain, sequence or polypeptide. Binding partners of use in the invention are typically those which are found in nature, or derivatives thereof, and exhibit natural modification-dependent binding to a binding domain, sequence or polypeptide of the invention as defined herein. In one embodiment of the invention, a binding partner is shorter (i.e., by at least one N-terminal or C-terminal amino acid) than the natural full-length polypeptide.

As used herein, the term "associates" or "binds" refers to a binding domain as described herein and its binding partner having a binding constant sufficiently strong to allow detection of binding by FRET or other detection means, which are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernable change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 $\mu$M (Kd). In many cases, the Kd will be in the mM range. The terms "complex", "dimer", "multimer" and "oligomer" as used herein, refer to the binding domain and its binding partner in the associated or bound state. More than one molecule of each of the two or more proteins may be present in a complex, dimer, multimer or oligomer according to the methods of the invention.

As used herein, the term "binding sequence" refers to that portion of a polypeptide comprising at least 4 or 6 amino acids, preferably at least 10, 20, 100 or 1000 contiguous (i.e., covalently linked by peptide bonds) amino acid residues or even as many residues as are comprised by a full-length protein, that are sufficient for modification-dependent binding to a binding partner. A binding sequence may exist on a polypeptide molecule that consists solely of binding sequence amino acid residues or may, instead, be found in the context of a larger polypeptide chain (i.e., one that comprises amino acids other than those of the binding sequence).

As used herein in reference to those binding sequences that are of use in the invention, the term "natural binding sequence" refers to a binding sequence, as defined above, which consists of an amino acid sequence which is found in nature and which is naturally dependent upon the modification state of a site for post-translational modification found within it for binding to a binding partner. A "natural binding sequence" may be present either in isolation or in the context of a larger polypeptide molecule, which molecule may be naturally occurring or recombinant. If present, amino acids outside of the binding sequence may be either natural, i.e., from the same polypeptide sequence from which the fragment is derived, or non-natural, i.e., from another (different) polypeptide, or non-natural (a sequence that is not derived from any known polypeptide). In the methods and transgenic organisms of the invention, a binding sequence and its binding partner generally exist on two different polypeptide chains.

However, the present invention is not limited to naturally occurring sequences, including allelic variants. Modifications may be made to the amino acid sequence of the binding domain and/or the binding partner, such as substitutions, deletions and/or insertions. In particular, such modifications may be made to identify important regions of the molecule with respect to, for example, protein-protein interactions.

As used herein, the term "binding polypeptide" refers to a molecule comprising multiple binding sequences, as defined above, which sequences are derived from a single, naturally-occurring polypeptide molecule and are both necessary and, in combination, sufficient to permit modification-state-dependent binding of the binding polypeptide to its binding partner, as defined above, wherein the sequences of the binding polypeptide are either contiguous or are non-contiguous. As used herein in reference to the component binding sequences of a binding polypeptide, the term "non-contiguous" refers to binding sequences which are linked by intervening naturally-occurring, as defined herein, amino acid sequences. The amino acids of a polypeptide that do not significantly contribute to the modification-state-dependent binding of that polypeptide to its binding partner may be those amino acids which are naturally present and link the binding sequences in a binding polypeptide or they may be derived from a different polypeptide. In the methods and transgenic organisms of the invention, a binding polypeptide and its binding partner (which may, itself, be a binding domain, sequence or polypeptide, as defined herein) typically exist on two different polypeptide chains.

It is preferred that the binding domain and/or binding partner comprise a sequence which directs modification of a site on the binding domain and/or binding partner by one or more of the following enzymes: a carbohydrate transferase (e.g., a UDP-N-Acetylglucosamine-Dolichyl-phosphate-N-acetylsglucosaminephospho transferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a glycylpeptide-N-tetradecanoyltransferase (peptide N-myristoyltransferase)), an NAD:Arginine ADP ribosyltransferase, a protease, a protein kinase or a phosphatase.

It is additionally preferred that the site permits addition of a chemical moiety which may be, for example: a ubiquitin moiety, a glycosyl moiety, an ADP-ribosyl moiety, a fatty acid moiety, a sentrin moiety or a phosphate group and the addition prevents binding of the binding domain to the binding partner.

As used herein the term "prevents binding" or "prevents association" refers to the ability of at least one of a ubiquitin moiety, a glycosyl moiety, a fatty acyl moiety, a sentrin moiety, an ADP-ribosyl moiety or a phosphate moiety to inhibit the association, as defined above, of a binding domain and a binding partner thereof by at least 10%, preferably by 25 to 50%, highly preferably by 75 to 90% and, most preferably, by 95–100% relative to the association observed in the absence of such a modification under the same experimental conditions.

According to another preferred embodiment, the site permits addition of a chemical moiety which may be for example: a ubiquitin moiety, a glycosyl moiety, an ADP-ribosyl moiety, a fatty acid moiety, a sentrin moiety or a phosphate moiety, and the addition promotes binding of the binding domain to the binding partner.

As used herein, the term "promotes binding" refers to that which causes an increase in binding of the natural binding domain and its binding partner of at least two-fold, preferably 10- to 20-fold, highly preferably 50- to 100-fold, more preferably from 200- to 1000-fold, and, most preferably, from 200 to 10,000-fold.

Preferably, the site permits removal of a chemical moiety which may be: a ubiquitin moiety, a glycosyl moiety, an ADP-ribosyl moiety, a fatty acid moiety, a sentrin moiety or a phosphate moiety, and the removal prevents binding of the binding domain to the binding partner.

It is preferred that the site permits removal of a chemical moiety which may be: a ubiquitin moiety, a glycosyl moiety, an ADP-ribosyl moiety, a fatty acid moiety, a sentrin moiety or a phosphate moiety, and the removal promotes binding of the isolated natural binding domain to the binding partner.

A binding domain useful in the present invention will comprise a binding site which will permit it to bind to other polypeptides (binding partners) to form a complex. Polypeptides are known to be able to associate in a number of ways, and domains which mediate polypeptide association are known in the art. For example, coiled coils, acid patches, zinc fingers, calcium hands, WD40 motifs, SH2/SH3 domains and leucine zippers are all polypeptide domains known to mediate protein-protein interactions, as are other domains known to those skilled in the art.

B. Detectable Labels

At least one, preferably both, of the binding domain and the binding partner comprise a detectable label, more preferably, the detectable label emits or absorbs Light and, most preferably, the light is fluorescent.

"Detectable label" in the context of the present invention means a polypeptide whose physical characteristics alter in a detectable manner depending on its molecular context, such as when the polypeptide to which it is linked binds to another polypeptide. It is particularly preferred that the detectable label is detectable in a non-invasive manner that does not require destruction of cellular material. Thus for example labels that require the extraction and resolution of cellular components and do not allow in situ measurements are preferably excluded. Radioactive labels are also preferably excluded.

However, in one embodiment, the detectable label may comprise subunits or fragments of enzymes that are functional when associated. For example, β-galactosidase may be cleaved into two fragments ($\Delta\alpha$ and $\Delta\omega$) which when expressed together form a functional enzyme (see Sambrook et al., ibid). Such a system has been used in intact yeast to monitor protein-protein interactions (Rossi et al., 1997, Proc. Natl. Acad. Sci. USA 94: 8405–8410). Also, bacterial luciferase can be produced as two fragments which when expressed together and associate, form a functional enzyme (Almashanu et al., 1996, Protein Eng. 9: 803-9).

Since the binding domain-label and binding partner-label polypeptides will be expressed by transgenic organisms from a construct present in the genome of the organism, the label will be in the form of a polypeptide whose amino acid constituents are naturally occurring amino acids, including those arising from post-translational modifications. The nucleic acid constructs encoding said polypeptides may be introduced into the genome of the organism as described below. Typically, the binding domain and binding partner is linked to the detectable label by being expressed in the form of a fusion protein. However, the binding domain and/or binding partner may be linked to their detectable label by any physiological applicable means. For example they may be part of a multi-protein complex joined by disulphide bonding or by non-covalent bonding, such as electrostatic interactions, hydrophobic interactions and/or van der Waal's forces.

Preferably, the changing physical characteristics may be detected in living cells using non-invasive techniques such as FRET. Thus in a preferred embodiment, the detectable label is a fluorescent protein.

"Fluorescent protein" refers to any protein which fluoresces when excited with appropriate electromagnetic radiation. This includes proteins whose amino acid sequences are either natural or engineered. A "fluorescent protein" is a full-length fluorescent protein or fluorescent fragment thereof.

It is contemplated that with regard to fluorescent labels employed in FRET, the reporter labels are chosen such that the emission wavelength spectrum of one (the "donor") is within the excitation wavelength spectrum of the other (the "acceptor").

Examples of fluorescent proteins which vary among themselves in excitation and emission maxima are listed in Table 1 of WO 97/28261. These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], 10c [513/527], W1B [432(453)/476(503)], Emerald [487/508] and Sapphire [395/511]. This list is not exhaustive of fluorescent proteins known in the art; additional examples are found in the Genbank and SwissProt public databases. Further examples are described in Matz et al., 1999 (Nature Biotech 17: 969–973) and include red fluorescent protein from *Discosoma* sp. (drFP583).

In a FRET assay of the invention, the fluorescent protein labels are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by a binding domain and its binding partner labeled with different fluorescent protein labels, wherein one is linked to a donor and the other to an acceptor label, in monitoring protein-protein interactions according to the present invention. A single polypeptide may comprises a blue fluorescent protein donor label and a green fluorescent protein acceptor label, wherein each is fused to a different assay component (i.e., in which one is fused to the binding domain and the other to its binding partner); such a construct is herein referred to as a "tandem" fusion protein.

Alternatively, two distinct polypeptides ("single" fusion proteins) one comprising or a natural binding domain and the other its binding partner may be differentially labeled with the donor and acceptor fluorescent protein labels, respectively. The construction and use of tandem fusion proteins in the invention can reduce significantly the molar concentration of peptides necessary to effect an association between differentially-labeled polypeptide assay components relative to that required when single fusion proteins are instead used. The labeled binding domain, sequence or polypeptide and/or its binding partner may be produced via the expression of recombinant nucleic acid molecules comprising an in-frame fusion of sequences encoding such a polypeptide and a fluorescent protein label in vivo, for example in a transgenic animal of the invention.

A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired. Nucleic acid sequences may, for example, be modified by virtue of the degeneracy of the genetic code to optimise the codon usage to take into account the codon bias in a given transgenic organism of interest.

The means by which a binding domain and its binding partner are assayed for association using fluorescent protein labels according to the invention may be briefly summarized as follows:

Whether or not the natural binding domain and its binding partner are present on a single polypeptide molecule, one is labeled with a green fluorescent protein, while the other is preferably labeled with a red or, alternatively, a blue fluorescent protein. Useful donor:acceptor pairs of fluorescent proteins (see WO97/28261) include, but are not limited to:

Donor: S72A, K79R, Y145F, M153A and T203I (excitation 395 nm; emission 511)

Acceptor: S65G, S72A, K79R and T203Y (excitation 514 nm; emission 527 nm), or T203Y/S65G, V68L, Q69K or S72A (excitation 515 nm; emission 527 nm).

An example of a blue:green pairing is P4-3 (shown in Table 1 of WO97128261) as the donor label and S65C (also of Table 1 of WO97/28261) as the acceptor label. The natural binding domain, sequence or polypeptide and corresponding binding partner are exposed to light at, for example, 368 nm, a wavelength that is near the excitation maximum of P4-3. This wavelength excites S65C only minimally. Upon excitation, some portion of the energy absorbed by the blue fluorescent protein label is transferred to the acceptor label through FRET if the natural binding domain, sequence or polypeptide and its binding partner are in close association. As a result of this quenching, the blue fluorescent light emitted by the blue fluorescent protein is less bright than would be expected if the blue fluorescent protein existed in isolation. The acceptor label (S65C) may re-emit the energy at longer wavelength, in this case, green fluorescent light By way of an example, after an event, such as an intracellular event, resulting in modification of one or both of the natural binding domain and its binding partner by a protein modifying enzyme, the natural binding domain and its binding partner (and, hence, the green and red or, less preferably, green and blue fluorescent proteins) physically separate or associate, accordingly inhibiting or promoting FRET. For example, if activity of the modifying enzyme results in dissociation of a protein:protein complex, the intensity of visible blue fluorescent light emitted by the blue fluorescent protein increases, while the intensity of visible green light emitted by the green fluorescent protein as a result of FRET, decreases.

Such a system is useful to monitor the activity of enzymes that modify a site for post-translational modification of a binding domain and, optionally, its binding partner to which the fluorescent protein labels are fused as well as the activity of protein modifying enzymes or candidate modulators thereof.

In particular, this invention contemplates assays in which the amount or activity of a modifying enzyme in one or more cells of a transgenic organism is determined by expressing a binding domain and its binding partner, differentially-labeled with fluorescent proteins, in the cells of the transgenic organisms, and measuring changes in fluorescence of the donor label, the acceptor label or the relative fluorescence of both Thus, fusion proteins, as described above, which comprise either one or both of the labeled natural binding domain and its binding partner of an assay of the invention can be used for, among other things, monitoring the activity of a protein modifying enzyme inside the cell that expresses the recombinant tandem construct or two different recombinant constructs.

Advantages of single-and tandem fluorescent protein/polypeptides comprising a binding domain fused to a fluorescent protein include the greater extinction coefficient and quantum yield of many of these proteins compared with those of the non-peptide fluorophores.

Thus, in a preferred embodiment, the enzyme of interest's substrate (i.e., the binding domain and, optionally, the corresponding binding partner), and reaction products (i.e., the binding domain and, optionally, the corresponding binding partner after modification) are both fluorescent but with different fluorescent characteristics.

In particular, the substrate and modified products exhibit different ratios between the amount of light emitted by the donor and acceptor labels. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, $Aequorea$-derived or-related fluorescent protein labels tend to be protease resistant. Therefore, they are likely to retain their fluorescent properties throughout the course of an experiment.

As described above, the donor fluorescent protein label is capable of absorbing a photon and transferring energy to another fluorescent label. The acceptor fluorescent protein label is capable of absorbing energy and emitting a photon. If needed, the linker connects the natural binding domain and its binding partner either directly or indirectly, through an intermediary linkage with one or both of the donor and acceptor fluorescent protein labels. Regardless of the relative order of the binding domain, its binding partner and the donor and acceptor fluorescent protein labels on a polypeptide molecule, it is essential that sufficient distance be placed between the donor and acceptor by the linker and/or the binding domain and its binding partner to ensure that FRET does not occur unless the binding domain and its binding partner bind. It is desirable, as described in greater detail in WO97/28261, to select a donor fluorescent protein label with an emission spectrum that overlaps with the excitation spectrum of an acceptor fluorescent protein label. In some embodiments of the invention the overlap in emission and excitation spectra will facilitate FRET. A fluorescent protein of use in the invention includes, in addition to those with intrinsic fluorescent properties, proteins that fluoresce due intramolecular rearrangements or the addition of cofactors that promote fluorescence.

For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, $Aequorea victoria$, from the sea pansy, $Renilla reniformis$, and from $Phialidium gregarium$. (Ward et al., 1982, Photochem. Photobiol., 35: 803–808;Levine et al., 1982, Comp. Biochem. Physiol.,72B: 77–85). See also Matz, et al., 1999, ibid for fluorescent proteins isolated recently from Anthoza species (accession nos. AF168419, AF168420, AF168421, AF168422, AF168423 and AF168424).

A variety of $Aequorea$-related GFPs having useful excitation and emission spectra have been engineered by modifying the amino acid sequence of a naturally occurring GFP from $Aequorea victoria$. (Prasher et al., 1992, Gene, 111: 229–233;Heim et al., 1994, Proc. Natl. Acad. Sci. U.S.A., 91: 12501–12504;PCT/US95/14692). As used herein, a fluorescent protein is an $Aequorea$-related fluorescent protein if any contiguous sequence of 150 amino acids of the fluorescent protein has at least 85% sequence identity with an amino acid sequence, either contiguous or non-contiguous, from the wild type $Aequorea$ green fluorescent protein (SwissProt Accession No. P42212). More preferably, a fluorescent protein is an $Aequorea$-related fluorescent protein if any contiguous sequence of 200 amino acids of the fluorescent protein has at least 95% sequence identity with an amino acid sequence, either contiguous or non-contiguous, from the wild type $Aequorea$ green fluorescent protein of SwissProt Accession No. P42212. Similarly, the fluorescent protein may be related to $Renilla$ or $Phialidium$ wild-type fluorescent proteins using the same standards.

$Aequorea$-related fluorescent proteins include, for example, wild-type (native) $Aequorea victoria$ GFP, whose nucleotide and deduced amino acid sequences are presented in Genbank Accession Nos. L29345, M62654, M62653 and others $Aequorea$-related engineered versions of Green Fluorescent Protein, of which some are listed above. Several of these, i.e., P4, P4-3, W7 and W2 fluoresce at a distinctly shorter wavelength than wild type.

C. Reporter Polypeptide Constructs

As stated above, recombinant nucleic acid constructs of particular use in the invention are typically those which comprise in-frame fusions of sequences encoding a binding domain or a binding partner therefor and a fluorescent protein. If a binding domain and its binding partner are to be expressed as part of a single polypeptide, the nucleic acid molecule additionally encodes, at a minimum, a donor fluorescent protein label fused to one, an acceptor fluorescent protein label fused to the other, a linker that couples the two and is of sufficient length and flexibility to allow for folding of the polypeptide and pairing of the natural binding domain, sequence or polypeptide with the binding partner, and gene regulatory sequences operatively linked to the fusion coding sequence. If single fusion proteins are instead encoded (whether by one or more nucleic acid molecules), each nucleic acid molecule need only encode a binding domain or a binding partner therefor, fused either to a donor or acceptor fluorescent protein label and operatively linked to gene regulatory sequences. Preferably, the fusion protein comprising the binding domain and the fusion protein comprising the binding partner are encoded by separate nucleic acid constructs.

"Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and a transcription termination sequence. The term "control sequences" is intended to include, at a minimum, components whose presence can influence expression, and can also include additional components whose presence is advantageous, for example, leader sequences and fusion partner sequences.

Particularly preferred regulatory sequences are those that confer tissue-specific or inducible expression. Tissue-specific expression may be used to confine expression of the binding domain and/or binding partner to a cell type or tissue/organ of interest. Inducible expression allows the researcher to control when expression of the polypeptides takes places. Thus, for example, a transgenic organism may be produced and cross-bred in the absence of expression of the binding domain and/or binding partner, and only when it is desired to monitor the interaction between the binding domain and binding partner is expression induced, by for example administering a compound that upregulates expression from the inducible regulatory construct.

Since the nucleic acid constructs are typically to be integrated into the host genome, it is important to include sequences that will permit expression of polypeptides in a particular genomic context. One possible approach would be to use homologous recombination to replace the endogenous gene encoding the binding protein or binding partner with a sequence encoding the corresponding polypeptide fused to a detectable label. This should ensure that the fusion polypeptide is subject to the same transcriptional regulatory mechanisms as the endogenous gene. Alternatively, homologous recombination may be used in a similar manner but with the regulatory sequences also replaced so that the fusion polypeptide is subject to a different form of regulation— such as inducible expression in the presence of an exogenously added compound.

However, if the construct is placed elsewhere in the genome, it is possible that the chromatin in that region will be transcriptionally silent and in a condensed state. If this occurs, then the labeled polypeptide will not be expressed— these are termed position-dependent effects. To overcome this problem, it may be desirable to include locus control regions (LCRs) that maintain the intervening chromatin in a transcriptionally competent open conformation. LCRs (also known as scaffold attachment regions (SARs) or matrix attachment regions (MARs)) are well known in the art—an example being the chicken lysozyme A element (Stief et al., 1989, Nature 341: 343), which can be positioned around an expressible gene of interest to effect an increase in overall expression of the gene and diminish position dependent effects upon incorporation into the organism's genome (Stief et al., 1989, supra). Another example is the CD2 gene LCR described by Lang et al., 1991, Nucl. Acid. Res. 19: 5851–5856.

Thus, a polynucleotide construct for use in the present invention, to introduce a nucleotide sequence encoding a binding domain comprising a detectable label or a binding partner comprising a detectable label into the genome of a multicellular organism,. typically comprises a nucleotide sequence encoding the binding domain or binding partner in-frame with a nucleotide sequence encoding a detectable sequence, both sequences being operatively linked to a regulatory sequence capable of directing expression of the coding sequences. In addition the polynucleotide construct may comprise flanking sequences homologous to the host cell organism genome to aid in integration. An alternative approach would be to use viral vectors that are capable of integrating into the host genome, such as retroviruses.

Preferably, a nucleotide construct for use in the present invention further comprises flanking LCRs.

D. Construction of Transgenic Organisms Expressing Binding Domains and Binding Partners Linked to Detectable Labels A transgenic organism of the invention and for use in the present invention is preferably a multicellular eukaryotic organism, such as an animal, a plant or a Fungus. Animals include animals of the phyla cnidaria, ctenophora, platyhelminthes, nematoda, annelida, mollusca chelicerata, uniramia, crustacea and chordata. Uniramians include the subphylum hexpoda that includes insects such as the winged insects. Chordates includes vertebrate groups such as mammals, birds, reptiles and amphibians. Particular examples of mammals include non-human primates, cats, dogs, ungulates such as cows, goats, pigs, sheep and horses and rodents such as mice, rats, gerbils and hamsters.

Plants include the seed-bearing plants angiosperms and conifers. Angiosperms include dicotyledons and monocotyledons. Examples of dicotyledonous plants include tobacco, (*Nicotiana plumbaginifolia* and *Nicotiana tabacum*), arabidopsis (*Arabidopsis thaliana*), *Aspergillus niger*, *Brassica napus*, *Brassica nigra*, *Datura innoxia*, *Vicia narbonensis*, *Vicia faba*, pea (*Pisum sativum*), cauliflower, carnation and lentil (*Lens culinaris*) Examples of monocotyledonous plants include cereals such as wheat, barley, oats and maize.

Production of Transgenic Animals

Techniques for producing transgenic animals are well known in the art. A useful general textbook on this subject is Houdebine, Transgenic animals—Generation and Use (Harwood Academic, 1997)—an extensive review of the techniques used to generate transgenic animals from fish to mice and cows.

Advances in technologies for embryo micromanipulation now permit introduction of heterologous DNA into, for example, fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., Manipulating the Mouse Embryo, (Cold Spring Harbor Press 1986); Krimpenfort et al., Bio/Technology 9:844 (1991); Palmiter et al., Cell, 41: 343 (1985); Kraemer et al., Genetic manipulation of the Mammalian Embryo, (Cold Spring Harbor Laboratory Press 1985); Hammer et al., Nature, 315: 680 (1985); Wagner et al., U.S. Pat. No. 5,175,385; Krimpenfort et al., U.S. Pat. No. 5,175,384, the respective contents of which are incorporated herein by reference Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology as described in Schnieke, A. E. et al., 1997, Science, 278: 2130 and Cibelli, J. B. et al., 1998, Science, 280: 1256. Using this method, fibroblasts from donor animals are stably transfected with a plasmid incorporating the coding sequences for a binding domain or binding partner of interest under the control of regulatory. Stable transfectants are then fused to enucleated oocytes, cultured and transferred into female recipients.

Analysis of animals which may contain transgenic sequences would typically be performed by either PCR or Southern blot analysis following standard methods.

By way of a specific example for the construction of transgenic mammals, such as cows, nucleotide constructs comprising a sequence encoding a binding domain fused to GFP are microinjected using, for example, the technique described in U.S. Pat. No. 4,873,191, into oocytes which are obtained from ovaries freshly removed from the mammal. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000 g to visualize the pronuclei for injection and then cultured from the zygote to morula or blastocyst stage in oviduct tissue-conditioned medium. This medium is prepared by using luminal tissues scraped from oviducts and diluted in culture medium. The zygotes must be placed in the culture medium within two hours following microinjection.

Oestrous is then synchronized in the intended recipient mammals, such as cattle, by administering coprostanol. Oestrous is produced within two days and the embryos are transferred to the recipients 5–7 days after estrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example in WO91/10741.
Production of Transgenic Plants Techniques for producing transgenic plants are well known in the art. Typically, either whole plants, cells or protoplasts may be transfected with a suitable nucleic acid construct encoding a binding domain or binding partner. There are many methods for introducing transforming DNA constructs into cells, but not all are suitable for delivering DNA to plant cells. Suitable methods include Agrobacterium infection (see, among others, Turpen et al., 1993, J. Virol. Methods, 42: 227–239) or direct delivery of DNA such as, for example, by PEG-mediated or liposome-mediated transformation, by electroporation or by acceleration of DNA coated particles. Acceleration methods are generally preferred and include, for example, microprojectile bombardment. A typical protocol for producing transgenic plants (in particular moncotyledons), taken from U.S. Pat. No. 5,874,265, is described below.

An example of a method for delivering transforming DNA segments to plant cells is microprojectile bombardment. In this method, non-biological particles may be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming both dicotyledons and monocotyledons, is that neither the isolation of protoplasts nor the susceptibility to Agrobacterium infection is required. An illustrative embodiment of a method for delivering DNA into plant cells by acceleration is a Biolistics Particle Delivery System, which can be used to propel particles coated with DNA through a screen, such as a stainless steel or Nytex screen, onto a filter surface covered with plant cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and may be too large for attaining a high frequency of transformation. This may be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one may obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step may include assaying cultures directly for a screenable trait or by exposing the bombarded cultures to a selective agent or agents.

An example of a screenable marker trait is the red pigment produced under the control of the R-locus in maize. This pigment may be detected by culturing cells on a solid support containing nutrient media capable of supporting growth at this stage, incubating the cells at, e.g., 18° C. and greater than 180 $\mu$E m$^{-2}$ s$^{-1}$, and selecting cells from colonies (visible aggregates of cells) that are pigmented. These cells may be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g. for one to two weeks) and transferred to filters overlaying solid medium containing from 1–3 mg/l bialaphos. While ranges of 1–3 mg/l will typically be preferred, it is proposed that ranges of 0.1–50 mg/l will find utility in the practice of the invention. The type of filter for use in bombardment is not believed to be particularly crucial, and can comprise any solid, porous, inert support.

Cells that survive the exposure to the selective agent may be cultured in media that supports regeneration of plants. Tissue is maintained on a basic media with hormones for about 2–4 weeks, then transferred to media with no hormones. After 2–4 weeks, shoot development will signal the time to transfer to another media.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 $\mu E$ $m^{-2}$ $s^{-1}$ of light. Plants are preferably matured either in a growth chamber or greenhouse. Regeneration will typically take about 3–12 weeks. During regeneration, cells are grown on solid media in tissue culture vessels. An illustrative embodiment of such a vessel is a petri dish. Regenerating plants are preferably grown at about 19° C. to 28° C. After the regenerating plants have reached the stage of shoot and root development, they may be transferred to a greenhouse for further growth and testing.

Genomic DNA may be isolated from callus cell lines and plants to determine the presence of the exogenous gene through the use of techniques well known to those skilled in the art such as PCR and/or Southern blotting.

The above mentioned techniques are typically used to produce a transgenic organism comprising, stably integrated into its germline tissues, a nucleotide sequence capable of directing the expression of a binding domain and/or binding partner, typically fused to a detectable marker, in one or more cells of the organism. Where the detectable label is not fused to the binding domain or binding partner as part of a contiguous polypeptide sequence (fusion protein) then the transgenic organism will also comprise, typically stably integrated into its germline tissues, a nucleotide sequence capable of directing the expression of a polypeptide comprising a detectable label that is capable of binding to the binding domain or binding partner without affecting the binding of the binding domain to the binding partner. However it is preferred to use fusion proteins.

In a preferred embodiment, a number of transgenic organisms may be produced, each expressing either a labeled binding domain or a labeled binding partner, but not both. One of these organisms that expresses a labeled binding domain may then be cross-bred with another organism that expresses a labeled binding partner to produce offspring that express both.

The transgenic multicellular organisms thus produced, may be used in the assay methods of the invention.

E. Methods by which to Detect Protein:Protein Binding in Assays of the Invention According to the invention, the association of the binding domain and binding partner is measured using label detection techniques that can determine the formation or destruction of protein:protein complexes. Of particular use in the invention are those methods which entail fluorescent labeling of the binding domain and/or its binding partner, and subsequent detection of changes in fluorescence, whether in frequency or level, when the binding domain interacts with its binding partner. Several such procedures are briefly summarized below.

Fluorescent Resonance Energy Transfer (FRET)

A tool with which to assess the distance between one molecule and another (whether protein or nucleic acid) or between two positions on the same molecule is provided by the technique of fluorescent resonance energy transfer (FRET), which is now widely known in the art (for a review, see Matyus, 1992, J. Photochem. Photobiol. B: Biol., 12: 323–337, which is herein incorporated by reference). FRET is a radiationless process in which energy is transferred from an excited donor molecule to an acceptor molecule; the efficiency of this transfer is dependent upon the distance between the donor and acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, Principles of Fluorescence Spectroscopy, Plenum Press, New York; Jovin and Jovin, 1989, Cell Structure and Function by Microspectrofluorometry, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a flurochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission specturm of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. However, in the context of the present invention, FRET is generally performed in vivo. According to the invention, a binding domain, sequence or polypeptide and its binding partner, comprised either by the same or by different polypeptide molecules, are differentially labeled, one with a donor and the other with an acceptor, and differences in fluorescence under different conditions measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent labels or a fluorescent label and a molecule known to quench its signal; differences in the proximity of the natural binding domain to its binding partner under different conditions can be gauged based upon a difference in the fluorescence spectrum or intensity observed.

This combination of protein-labeling methods and devices confers a distinct advantage over prior art methods for determining the association of polypeptides, optionally dependent on the activity of protein-modifying enzymes, as described above, in that results of all measurements are observed in real time (i.e., as a reaction progresses). This is significantly advantageous, as it allows both for rapid data collection and yields information regarding reaction kinetics under various conditions.

A sample assayed according to the invention therefore comprises a mixture at equilibrium of the labeled natural binding domain and its binding partner which, when disassociated from one another, fluoresce at one frequency and, when complexed together, fluoresce at another frequency or, alternatively, of molecules which either do or do not fluoresce depending upon whether or not they are associated.

The binding domain and/or binding partner therefor is typically fused in-frame with a fluorescent protein, as described below. The choice of fluorescent label will be such that upon excitation with light, labeled peptides which are associated will show optimal energy transfer between fluorophores. In the presence of a protein modifying enzyme that recognizes the site for -protein modification present on the natural binding domain and, optionally, the binding partner, the natural binding domain and its binding partner dissociate due to a structural or electrostatic change which occurs as a consequence of addition or removal of a chemical moiety, as described herein, to/from the enzyme recognition site, thereby leading to a decrease in energy transfer and increased emission of light by the donor fluorophore. In this way, the state of polypeptide association/modification can be monitored and quantitated in real-time.

A number of parameters of fluorescence output are envisaged including 1. measuring fluorescence emitted at the emission wavelength of the acceptor (A) and donor (D) and determining the extent of energy transfer by the ratio of their emission amplitudes;
2. measuring the fluorescence lifetime of D;
3. measuring the rate of photobleaching of D; or
4. measuring the anisotropy of D and/or A.

Certain of these techniques are presented below.

Alternative Fluorescent Techniques Suitable for Monitoring Protein:Protein Binding in Assays of the Invention Additional embodiments of the present invention are not dependent on FRET. For example the invention can make use of fluorescence correlation spectroscopy (FCS), which relies on the measurement of the rate of diffusion of a label (see Elson and Magde, 1974 Biopolymers, 13: 1–27;Rigler et al., 1992, in Fluorescence Spectroscopy: New Methods and Applications, Springer Verlag, pp.13–24;Eigen and Rigler, 1994, Proc. Natl. Acad Sci. U.S.A., 91: 5740–5747;Kinjo and Rigler, 1995, Nucleic Acids Res., 23: 1795–1799).

In FCS, a focused laser beam illuminates a very small volume of solution, of the order of $10^{-15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide will diffuse at a slower rate if it is large than if it is small. Thus, multimerized polypeptides will display slow diffusion rates, resulting in a lower number of fluorescent bursts in any given timeframe, while labeled polypeptides which are not multimerized or which have dissociated from a multimer will diffuse more rapidly. Binding of polypeptides according to the invention can be calculated directly from the diffusion rates through the illuminated volume.

Where FCS is employed, rather than FRET, it is not necessary to label more than one polypeptide. Preferably, a single polypeptide member of the multimer is labeled. The labeled polypeptide dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, Principles of Fluorescence Spectroscopy, Plenum Press, New York, incorporated herein by reference (see, for example, page 167).

Fluorescence anisotropy relies on the measurement of the rotation of fluorescent groups. Larger multimers of polypeptides rotate more slowly than monomers, allowing the formation of multimers to be monitored.

F. Protein Modifications in Assays of the Invention

The invention provides methods for assaying the activity of enzymes which perform post-translational modification of proteins in vivo. Table 1 lists some non-limiting examples of post-translational modifications.

TABLE 1

| Modification | Protein Source | Consensus Sequence/ Sequence | Reference/ GenBank No. |
|---|---|---|---|
| | | Modified residues indicated in bold. Residues forming part of the recognition site are shown in italics. | |

TABLE 1-continued

| Modification | Protein Source | Consensus Sequence/ Sequence | Reference/ GenBank No. |
|---|---|---|---|
| ADP-Ribosylation | B-50 | $^1$MLCCMRRTKQV EKND DD | Coggins et al., 1993, J. Neurochem., 60: 368–71 |
| | γ subunit of cGMP phosphodiesterase | $^{30}$FKQRQTRQFK | X04270 |
| Ubiquitination | I B | $^1$MFQAAERPQEW AMEG PRDGLKKERLLD DRH | M69043 |
| N-Myristoylation | Src | $^1$GSSKSKPKD | Resh, 1994, Cell, 76: 411–413 |
| | Lyn | $^1$GCIKSKRKD | Resh, 1994, supra |
| | Yes | $^1$GCIKSKEDK | Resh, 1994, supra |
| | Fyn | $^1$GCVQCKDKE | Resh, 1994, supra |
| | Gα | $^1$GCTLSAEDK | Resh, 1994, supra |
| Palmitylation | Lyn | $^1$GCIKSKRKD | M64608 |
| | Fyn | $^1$GCVQCKDKE | M14676 |
| | Gαi2 | $^1$GCTLSAEDK | Milligan et al., 1995, Trends Biochem. Sci., 20: 181–186 |
| N-Glycosylation | | -NXS/T- X can be any amino acid except P | Shakineshleman, 1996, Trends Glyco science and Glyco tech., 8: 115–130 |
| O-Glycosylation | p67$^{SRF}$ | $^{274}$GTTSTIQTAP$^3$ $^{13}$SAVSSADGTVL K$^{374}$DSSTDLTQTS SSGTVTLP | J03161 |
| Sentrinization | RanGAP1 | | Johnson and Hochstrasser,1997, Trends Cell.Biol., 7: 408–413 |
| | PML | | Kamitani et al., 1998. J. Biol. Chem., 273: 3117–3120 |

Phosphorylation—Kinase and Phosphatases

A particularly important post-translational modification for which a large number of enzymes and targets have been identified is phoshorylation and dephosphorylation. The art is replete with references to said enzymes, i.e. protein kinases and phosphatases, and their targets, including consensus phosphorylation motifs (such as -SQ- or -TQ- for the DNA dependent protein kinase (DNA-PK).

Some non-limiting examples of kinases and their sites for post-translational modification are presented in Table 2 (phosphorylation/dephosphorylation)

TABLE 2

| Kinase | Consensus Sequence | GenBank No./Reference |
|---|---|---|
| cAMP-dependent protein kinase | -RRXRRXS/T- | Cα subunit M34181 RIIβ subunit M31158 Trends in Biochem. Sci. (1990) 15 342–346. |
| Myosin Heavy Chain kinase | -KXXSX- | |
| Myosin Heavy Chain kinase | -RXT- | M93393 |
| Calmodulin-Dependent protein kinase II | -RXXSX- | α chain J02942 β chain M16112 γ chain J05072 δ chain J04063 |
| cGMP-dependent protein kinase | -XSRX- | β isozyme Y07512 |
| Protein kinase C | -XRXXSXRX- | Trends in Biochem. Sci.(1990) 15 342–346. |

TABLE 2-continued

| Kinase | Consensus Sequence | GenBank No./Reference |
|---|---|---|
| S6 kinase II | -XRXXSX- | α2 isozyme L07599, L07601 |
| dsRNS kinase pp68 | -SELSRR- | Trends in Biochem. Sci. (1990) 15 342–346. |
| Casein kinase I Mammary gland casein kinase | -XSXXSX- -XSXEX- | α isoform X80693 Trends in Biochem. Sci.(1990) 15 342–346. |
| Glycogen synthase kinase 3 | -XSXXXSX | α isoform L40027 |

X signifies any amino acid. Consensus sequences are taken from Trends Biochem Sci. (1990) 15: 342–346.

Further examples of protein kinases identified to date include the protein tyrosine kinase subfamily (such as PDGF receptors, EGF receptors, src family kinases (see Brown and Cooper, 1996, Biochimica and Biophysica Acta 1287: 121–149 for a review), the JAK kinase family (such as JAK1, JAK2 and tyk2), Erb B2, Bcr-Abl, Alk, Trk, Res/Sky—for a detailed review see Al-Obeidi et al., 1998, Biopolymers (Peptide Science), Vol 47: 197–223), the MAP kinase pathway subfamily (such as the MAP family, the ERK family, the MEK family, the MEKK family, RAF-1 and JNK), the cyclin-dependent kinase subfamily (such as p34$^{cdc2}$ and cdk2—see Nigg, 1995, Bioessays 17: 471–480 for a review), Wee1/Myt1, polo-like kinases (such as plk1, Plx1, POLO, Snk, Fnk/Prk Sak-a, Sak-b—see Lane and Nigg, 1997, Trends in Cell Biol. 7: 63–68), the receptor serine kinase subfamily, protein kinase C (PK-C), cyclic-AMP dependent kinase (PK-A), cyclic-GMP dependent kinase, Ca2+/calmodulin dependent kinases (such as CaM kinase I, II and IV), DNA dependent protein kinase,), phosphoinositide 3-kinases, PDK-1, the p21-activated protein kinase family (PAKs), such as Pak1, Pak2 and Pak3—see Sells and Chemoff, 1997, Trends in Cell Biol. 7: 162–167), p70 S6 kinase, IkB kinase, casein kinase II, glycogen-synthase kinases.

A discussion of particular kinase pathways involved in signal transduction is given in chapter 35 of Lewin, 1997, Gene VI, Oxford University Press.

Details of recognition and binding domains for a variety of kinases are given in Kuriyan and Cowburn, 1997, Annu. Rev. Biophys. Biomol. Struc. 26:259–288.

Some specific examples of kinases whose activity may be studied using the methods of the invention include the src family tyrosine kinases Lck and Fyn, that phosphorylate the TCR ζ chain, and are known to be involved in signal transduction associated with T cell receptor stimulation. The TCR ζ chain comprises specific tyrosine residues present in immunoreceptor tyrosine-based activation motifs (ITAMs) that are phosphorylatd by Lck and Fyn (Kuriyan and Cowburn, 1997, ibid.). The SH2 domain of another tyrosine kinase, ZAP70 binds to phosphorylated TCR ζ. Thus TCR ζ ITAM and ZAP70 SH2 represent binding domains and binding partners that may be of interest in studying the activity of the kinases Lck and Fyn (see Elder et al., 1994, Science 264: 1596–1599 and Chan et al., 1994, Science 264: 1599–1601.

Another example is the IgE receptor γ subunit and the SH2 domain of Syk that may be used to study the activity of the Lyn kinase.

Examples of phosphatase identified to date fall into three main families (for review see Barford et al., 1998, Annu. Rev. Biophys. Biomol. Struc. 27: 133–164). The PPP family includes the following catalytic subunits: PP1c, PP2Ac, PP2B, PPP1, PPP2A and PPP5 and the following regulatory subunits: NIPP-1, RIPP-1, p53BP2, $\gamma_1$34.5, PR65, PR55, PR72, PTPA, SV40 small T antigen, PPY, PP4, PP6 and PP5.

The PPM family includes pyruvate dehydrogenase phosphatase and *Arabidopsis* ABI1.

The protein tyrosine phosphatase family includes PTP1B, SHP-1, SHP-2 (cytosolic non-receptor forms), CD45 (see Thomas and Brown, 1999, Trends in Immunol, 20: 406 and Ashwell and D'Oro, 1999, Trends in Immunol, 20: 412 for further details), RPTP (receptor-like, transmembrane forms) and cdc25, kinase-associated phosphatase and MAP kinase phosphatase-1 (dual-specificity phosphatases). PTP1B is known to associate with the insulin receptor in vivo (Bandyopadhyay et al., 1997, J. Biol. Chem. 272: 1639–1645).

A simple FRET assay based upon these modifications to site for post-translational modification present on a natural binding domain may be performed as presented below.

TABLE 3

| Modification | Enzyme | Specific Action | GenBank No./Reference |
|---|---|---|---|
| Mono-ADP-Ribosylation | NAD: Arginine ADP-ribosyl transferase | | Zolkiewska et al., 1992, PNAS B2: 11352–6 |

TABLE 3-continued

| Modification | Enzyme | Specific Action | GenBank No./Reference |
|---|---|---|---|
| Poly-ADP-Ribosylation | Drosophila PARP | | D13806, D13807, D13808 |
| Ubiquitination | E1 E2 (UBC8) E3 (RSP5) | Ubiquitination of large subunit of RNA pol II (Rpb 1) (NB, E2 and E3 confer substrate specificity on the ubiquitination) | X55386, X56507, M65083, U18916, L11119, L11120, U00092, U75972 |
| N-Myristoylation | Glycylpeptide-N-tetra decanoyl-transferase (peptide N-myristoyl transferase) | | M86707 |
| N-Glycosylation | UDP-N-acetylglucosamine-dolichyl-phosphate N-acetylglucosamine phosphotransferase | Initial step in synthesis of dolichol-P-P-oligosacharides | X65603, S41875 |
| O-Glycosylation | O-GlcNAc transferase | | Kreppel et al., 1997, J. Biol. Chem., 272: 9308–9315 |
| Sentrinization | Ubc9 | | Gong et al., 1997, J. Biol. Chem., 272, 28198–28201 |
| (de) phosphorylation | Kinase/phosphatase | | See above | where NBD=natural binding domain; M=modification; F1=donor fluorophore and F2=acceptor fluorophore Alternatively, a FRET-based assay may follow a format such as:

(F1-NBD)(F2-partner) + substrate → F1-M-NBD + F2-partner + byproduct
    (FRET)                                       (No FRET)

Table 3 provides a non-limiting list of enzymes that are representative of some of the classes of modifying enzymes discussed herein as being amenable to assay according to the invention.

F1-NBD + F2-partner + substrate → (F1-M-NBD)(F2-partner) + byproduct
    (No FRET)                                     (FRET)

The several types of post-translational modification presented above will be discussed in some detail below, along with assays to test the enzymes that perform such modifications using natural binding domains and binding partners therefor according to the invention.

ADP-Ribosylation

Mono-ADP-ribosylation is a post-translational modification of proteins which is currently thought to play a fundamental role in cellular signalling. A number of mono-ADP-ribosyl-transferases have been identified, including endogenous enzymes from both bacterial and eukaryotic sources and bacterial toxins. A mono-ADP-riboylating enzyme, using as substrates the protein to be modified and nicotinamide adenine dinucleotide ($NAD^+$), is NAD:Arginine ADP ribosyltransferase (Zolkiewska et al., 1992, Proc. Natl. Acad. Sci. U.S.A., 89: 11352–11356). The reactions catalyzed by bacterial toxins such as cholera and pertussis toxin are well understood; the activities of these toxins result in the permanent modification of heterotrimeric G proteins. Endogenous transferases are also thought to modify G proteins and therefore to play a role in signal transduction in the cell (de Murcia et al., 1995, Trends Cell Biol., 5: 78–81). The extent of the effects that ADP-ribosylation can mediate in the cell is illustrated by the example of brefeldin A, a fungal toxin metabolite of palmitic acid. This toxin induces the mono-ADP-ribosylation of BARS-50 (a G protein involved in membrane transport) and glyceraldehyde-3-phosphate dehydrogenase. The cellular effects of brefeldin A include the blocking of constitutive protein secretion and the extensive disruption of the Golgi apparatus. Inhibitors of the brefeldin A mono-ADP-ribosyl-transferase reaction have been shown to antagonise the disassembly of the Golgi apparatus induced by the toxin (Weigert et al., 1997, J. Biol. Chem., 272: 14200–14207). A number of amino acid residues within proteins have been shown to function as ADP-ribose acceptors. Bacterial transferases have been identified which modify arginine, asparagine, cysteine and diphthamide residues in target proteins. Endogenous eukaryotic transferases are known which also modify these amino acids, in addition there is evidence that serine, threonine, tyrosine, hydroxyproline and histidine residues may act as ADP-ribose acceptors but the relevant transferases have not yet been identified (Cervantes-Laurean et al., 1997, Methods Enzymol., 280: 275–287 and references therein).

Poly-ADP-ribosylation is thought to play an important role in events such as DNA repair, replication, recombination and packaging and also in chromosome decondensation. The enzyme responsible for the poly-ADP-ribosylation of proteins involved in these processes is poly (ADP-ribose) polymerase (PARP; for *Drosophila melanogaster* PARP, see Genbank Accession Nos. D1 3806, D1 3807 and D13808). The discovery of a leucine zipper in the self-poly(ADP-ribosyl)ation domain of the mammalian PARP (Uchida et al., 1993, Proc. Natl. Acad. Sci. U.S.A., 90: 3481–3485) suggested that this region may be important for the dimerization of PARP and also its interaction with other proteins (Mendoza-Alvarez et al., 1993, J. Biol. Chem., 268: 22575–22580).

Specific examples of ADP-ribosylation sites are those found at $Cys_3$ and $Cys_4$ (underlined) of the B-50 protein (Coggins et al., 1993, J. Neurochem., 60: 368–371; SwissProt Accession No. P06836): ML CCMRRTKQVEKNDDD and Pγ (the γ subunit of cylic CMP phophodiesterase; Bondarenko et al., 1997, J. Biol. Chem., 272: 15856–15864; Genbank Accession No. X04270): FKQRQTRQFK.

Two non-limiting examples of assays of enzymatic activity according to the invention which assays are based upon the detection of changes in ADP-ribosylation-dependent protein:protein binding are briefly summarized as follows:

Assay 1:

This assay employs as reporter molecules the following:

Retinal rod cGMP phosphodiesterase subunit (P; whole protein, or as little as amino acids 19–87, mutated to remove the phosphorylation site at $Thr_{22}$; Bondarenko, 1997, J. Biol. Chem., 272: 15856–15864; Tsuboi et al., 1994, J. Biol. Chem., 269: 15016–15023; OWL accession no. P04972; Genbank accession no. X04270)

Transducin subunit (T; whole protein, or as little as amino acids 293–314, acetyl-EDAGNYIKVQFLELNMRRDVKE-amide; Rarick et al., 1992, *Science*, 256:1031–1033; OWL accession no. P04695; Genbank no. K03254)

These proteins are components of the vertebrate light-response system, which includes transducin (a heterotrimeric G protein), a cGMP-specific phosphodiesterase (PDE) and rhodopsin. Analogous components can be identified in a number of G protein-coupled signalling systems. T-GTP activates its effector, cGMP-PDE, by binding to the inhibitory subunits of that protein and thereby relieving inhibition its enzymatic activity (Stryer, 1986, Ann. Rev. Cell Biol., 2: 391–419). It has been shown that the ADP-ribosylation of P at $Arg_{33}$ or $Arg_{36}$ occurs when P is complexed with P but not when it is complexed with T (Bondarenko et al., 1997, supra). It has been suggested that the sites of ADP-ribosylation are masked in the P-T complex. This assay for ADP-ribosylation can be adapted to detect the de-ADP-ribosylation of P. Problems arise because the affinity of P for its alternative partners is affected by other factors including the nucleotide bound to T (T-GTP has higher affinity for P than does T-GDP) and the phosphorylation state of P. This can be overcome by using a T peptide to avoid the effects of nucleotide exchange and by using a P peptide lacking the relevant phosphorylation site ($Thr_{22}$; Tsuboi et al., 1994, supra). An 4/6 loop peptide (amino acids 293–314) has a high affinity for P (Noel et al, 1993, *Nature*, 366: 654–663). The ability of this system to be used as an assay for the ADP-ribosylation reaction depends upon the affinity of the T peptide (amino acids 293–314) for P (amino acids 19–87). If binding is too tight, a shorter peptide which has also been reported to stimulate PDE activity (i.e. associate with P; Rarick et. al., 1992, supra) can be used instead.

The design for such an assay is:

(T-F1)(P-F2)+NAD$^+$T-F1+(ADP-ribose)P-F2FRET No FRET where F1 is the donor fluorophore and F2 is the acceptor.

GFP or another fluorescent protein can be fused to a natural binding domain, sequence or polypeptide and/or its binding partner at either of the C- and N-termini of the two molecules followed by empirical detection of the labeled polypeptides in control protein binding reactions.

Assay 2:

The following component is employed in a homodimerization assay:

*Drosophila* PARP or a homologue thereof (whole protein or amino acids 369–994, lacking the zinc finger DNA binding domain; Uchida et al., 1993, *Proc. Natl. Acad. Sci. U.S.A.*, 90: 3481–3485; OWL accession no. P35875; Genbank accession nos. D13806, D13807 and D13808).

*Drosophila* PARP possesses a leucine zipper motif in the self-poly(ADP-ribosyl)ation domain which is also found in the bovine, mouse, chicken and human sequences. Two conserved glutamate residues are predicted to be poly(ADP-ribosylation) auto-modification sites. It has been suggested that poly(ADP-ribosylation) of these sites results in dissociation of the dimer due to the large negative charge of the polymer (Mendoza-Alvarez et al., 1993, supra). A catalytic dimer is required for the reaction to proceed as the auto-modification reaction has been shown to be intermolecular (Mendoza-Alvarez et al., 1993, supra). The leucine zipper domain is predicted to also mediate heterodimerization of PARP; thus, other poly(ADP-ribosylating) binding partners may be useful in this assay of the invention.

Thus the assay would be:

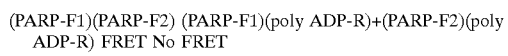

(PARP-F1)(PARP-F2) (PARP-F1)(poly ADP-R)+(PARP-F2)(poly ADP-R) FRET No FRET

Active dimer Inactive monomers where F1 is the donor fluorophore and F2 is the acceptor.

The fluorescent protein (e.g., GFP) is typically placed at the N-terminus of the truncated PARP molecule.

Ubiquitination

Ubiquitination of a protein targets the protein for destruction by the proteosome. This process of destruction is very rapid ($t_{1/2}$~60 seconds), and many proteins with rapid turnover kinetics are destroyed via this route. These include cyclins, p53, transcription factors and transcription regulatory factors, among others. Thus, ubiquitination is important in processes such as cell cycle control, cell growth, inflammation, signal transduction; in addition, failure to ubiquitinate proteins in an appropriate manner is implicated in malignant transformation. Ubiquitin is a 76-amino-acid protein which is covalently attached to a target protein by an isopeptide bond, between the a-amino group of a lysine residue and the C-terminal glycine residue of ubiquitin. Such modification is known as mono-ubiquitination, and this can occur on multiple Lys residues within a target protein.

Once attached, the ubiquitin can itself be ubiquitinated, thus forming extended branched chains of polyubiquitin. It is this latter state which signals destruction of the target protein by the proteosome. In the process of destruction, it appears that the polyubiquitinated protein is taken to the proteosome via a molecular chaperone protein, the ubiquitin molecules are removed undamaged (and recycled) and the target is degraded.

Ubiquitination is a complex process, which requires the action of three enzymes: Ubiquitin activating enzyme E1 (for human, Genbank Accession No. X56976), ubiquitin conjugating enzyme E2, also referred to as the ubiquitin carrier protein, (for human 17 kDa form, Genbank Accession No. X78140) and Ubiquitin protein ligase E3 (UBR1; human, Genbank Accession No. AF061556). There are multiple forms of each of these enzymes in the cell, and the above examples are, therefore, non-limiting.

An example of a ubiquitination site in a natural protein, IκB (Dai et al., 1998, J. Biol. Chem, 273: 3562–3573; Genbank Accession No. M69043) is as follows:

IκB NH$_3$-MFQAAERPQEWAMEGPRDGL
<u>K</u>KERLLDDRH—COOH where the ubiquitinated lysine residue is underlined.

According to the invention, a ubiquitination assay measures the addition of ubiquitin to, rather than the destruction of, a natural binding domain, sequence or polypeptide NFκB is a transcription factor held in the cytoplasm by the tight association with an inhibitor protein IκB., or other members of this protein family (Baldwin, 1996, Ann. Rev. Biochem., 14: 648–681). A variety of signals prompt the release of NFκB from IκB and the subsequent movement of NFκB to the nucleus, where it functions as a transcription factor. IκB is the first phosphorylated on two residues ($Ser_{32}$ and $Ser_{36}$), which prompts the ubiquitination of IκB on $Lys_{21}$ and other residues; such modification marks IκB for destruction by the proteosome (Dai et al, 1998, J. Biol. Chem., 273: 3562–3573). It has been suggested that following ubiquitination of IκB, a molecular chaperone protein VCP binds to IκB and displaces NFκB (Dai et al., 1998, supra), after which it is surmised that VCP transports IκB to the proteosome for destruction A fragment of IκB (amino acids 1–242) can participate in the early stages of the above process (i.e., it becomes phosphorylated and ubiquitinated, and binds VCP), but is not then destroyed by proteolysis (Dai, et al., 1998, supra).

A typical configuration for an assay for ubiquitination, in this non-limiting example using the natural binding domains found in this pathway, would be:

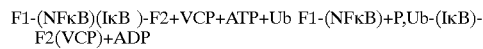

F1 is the donor fluorophore, F2 the acceptor, P is the phosphorylation and Ub is ubiquitin.

If the assay is to be constructed using fragments of the full length proteins, those which comprise natural binding domains (i.e., those which are "binding sequences", as defined above) then the regions of NFκB and IκB of interest are:

For the NFκB p65:p50 heterodimer: p65 (amino acids 12–317) as described as capable of binding IκB (Jaffray et al., 1995, Mol. Cell. Biol., 15: 2166–2172). p50 (amino acids 39–364; Ghosh et al., 1995, Nature, 373: 303–310). This represents the murine sequence (Accession No. M57999, M37732). As an alternative, the human p50 (amino acids 2–366; Muller et al., 1995, Nature, 373: 311–317) can be employed.

For IκB and VCP: IκB (amino acids 1–305; as deduced from the data of Bell et al., 1996, Mol. Cell. Biol., 16: 6477–6485). The amino acid sequence of IκB has been described (Davis et al., 1991, Science, 253: 1268–1271). The acidic domain of Iκc, which includes residues 275–300, is required for effective binding to NFκB. VCP, which is an optically inactive part of this assay (i.e. not fluorescently labeled), is used as a whole protein, as functional dissection of VCP has not been described to date. Typically, the VCP is endogenous to the cells of the organism and therefore need not be introduced into the transgenic organism.

For p50 of NFκB (murine amino acids 39–364, human amino acids 2–366 or, alternatively, an intact human or murine protein), the fluorescent protein is typically fused at the C-terminus of P50. As IκB binds at the C-terminus of NFκB, the fluorescent protein (e.g., GFP) needs to be in close proximity to the binding site.

For IκB (full protein or amino acids 1–305) the fluorescent protein is placed at the C-terminus. NFκB binds at the C-terminus of IκB; therefore, the fluorescent protein should be close to the binding site.

Other configurations include using labelled target polypeptide (such as VCP) wherein only one of NFκB or IκB are labelled but not both.

Glycosylation

N-linked glycosylation is a post-translational modification of proteins which occurs in the endoplasmic reticulum and golgi apparatus and is utilized with some proteins en route for secretion or destined for expression on the cell surface or in another organelle. The carbohydrate moiety is attached to Asn residues in the non-cytoplasmic domains of the target proteins, and the consensus sequence (Shakineshleman, 1996, Trends Glycosci. Glycotech., 8: 115–130) for a glycosylation site is NxS/T, where x cannot be proline or aspartic acid.

N-linked sugars have a common five-residue core consisting of two GlcNAc residues and three mannose residues due to the biosynthetic pathway. This core is modified by a variety of Golgi enzymes to give three general classes of carbohydrate known as oligomannosyl, hybrid and lactosamine-containing or complex structures (Zubay, 1998, Biochemistry, Wm. C. Brown Publishers). An enzyme known to mediate N-glycosylation at the initial step of synthesis of dolichyl-P-P-oligosaccharides is UDP-N-Acetylglucosamine-Dolichyl-phosphate-N-acetylsglucosamine phosphotransferase (for mouse, Genbank Accession Nos. X65603 and S41875).

Oxygen-linked glycosylation also occurs in nature with the attachment of various sugar moieties to Ser or Thr residues (Hansen el al, 1995, Biochem. J., 308: 801–813).

Complex O-linked glycosylation can be broken into at least six classes—mucin type, ser-1-GlcNAc; proteoglycan type, ser-Gal-Gal-Xyl core; collagen type hydroxylys-Gal-Glc; clotting factor type, ser-Xyl-Glc or ser-Xyl-Xyl-Glc core; fungal type, ser-Man; plant type, hydroxypro-Ara or ser-Gal (where GlcNAc=N-acetylglucosamine, Gal=galactose, Xyl=Xylose; Glc=glucose, Man=mannose and Ara= arabinose; Hansen et al., 1995, supra). Intracellular proteins are among the targets for O-glycosylation through the dynamic attachment and removal of O-N-Acetyl-D-glucosamine (O-GlcNAc; reviewed by Hart, 1997, Ann. Rev. Biochem., 66: 315–335). Proteins known to be O-glycosylated include cytoskeletal proteins, transcription factors, the nuclear pore protein complex, and tumor-suppressor proteins (Hart, 1997, supra). Frequently these proteins are also phosphoproteins, and there is a suggestion that O-GlcNAc and phosphorylation of a protein play reciprocal roles. Furthermore, it has been proposed that the glycosylation of an individual protein regulates protein:protein interactions in which it is involved.

Specific sites for the addition of O-GlcNAc are found, for example, at $Ser_{277}$, $Ser_{316}$ and $Ser_{383}$ of $p67^{SRF}$ (Reason et al., 1992, J. Biol. Chem., 267: 16911–16921; Genbank Accession No. J03161). The recognition sequences encompassing these residues are shown below:

$^{274}$GTT$\underline{S}$TIQTAP$^{313}$SAV$\underline{S}$SADGTVLK$^{374}$D$\underline{S}$STDLTQT $\underline{S}$SSGTVTLP The identity of sites of O-GlcNAc is additionally known for a small number of proteins including c-myc ($Thr_{58}$, also a phosphorylation site; Chou et al., 1995, J. Biol. Chem., 270: 18961–18965), the nucleopore protein p62 (see Reason et al., 1992, supra): MAGGPADT$\underline{S}$DPL and band 4.1 of the erythrocyte (see Reason et al., 1992, supra): AQTIT$\underline{S}$ETPSSTT.

The site at which modification occurs is, in each case, underlined. The reaction is mediated by O-GlcNAc transferase (Kreppel et al., 1997, J. Biol. Chem., 272: 9308–9315).

Several non-limiting examples of assay formats useful in the monitoring of glycoslating enzymes according to the invention may be summarized as follows:

Assay 1:

The reporter polypeptides of a first glycosylation assay are:

Chicken hepatic lectin (amino acids 49–207, predicted extracellular domain; Burrows el al, 1997, Biochem. J., 324: 673–680; OWL accession no. P02707; Genbank accession no. M63230)

c-Myc (amino acids 1–143, N-terminal transactivation domain; Chou et al., 1995, J. Biol. Chem., 270: 18961–18965; OWL accession no. P01107; Genbank accession no. V00568)

Chicken hepatic lectin (CHL) is a type II transmembrane protein which shows almost complete specificity for N-acetylglucosamine, which residue it binds by the C-terminal, extracellular carbohydrate-recognition domain (CRD). The intact receptor probably consists of a trimer of polypeptides stabilized by a coiled-coil structure formed by the transmembrane region and the stalk immediately N-terminal to the (CRD). Molecular modeling suggests, however, that the sugar-binding site is formed by a single polypeptide (Burrows at al., 1997,supra). It is likely that glycosylated c-Myc will bind to the O-GlcNAc at $Thr_{58}$.

c-Myc is a proto-oncogene product playing a role in the control of gene transcription. Mutation or deregulation of the expression of this protein can contribute. to malignant transformation of cells. The O-GlcNAcylation of c-Myc at $Thr_{58}$ is thought to be reciprocal to phosphorylation at this site which is also a site of frequent mutation in human lymphomas (Chou et al., 1995, supra).

In addition to its utility in enzymatic assays of the invention, this assay for O-Glc-NAcylation can be adapted to monitor the modification of the large number of cytoplasmic and nuclear proteins thought to undergo O-Glc-NAcylation (Hart, 1997, Ann. Rev. Biochem., 66: 315–35).

Thus, the assay would be:

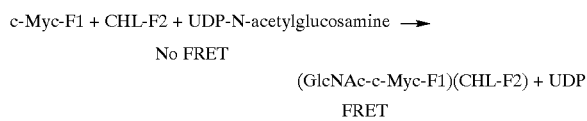

where F1 is the donor fluorophore, and F2 the acceptor fluorophore.

In reporter molecules of this glycosylation assay, a fluorescent protein (e.g., Green Fluorescent Protein, GFP) would typically be placed at the C-terminus of the CHL domain and probably at the N-terminus of the c-Myc transactivation domain. Because in the c-Myc transactivation domain the site of glycosylation is almost equidistant in primary structure from the termini, the most appropriate site would need to be determined empirically in the absence of structural information.

Assay 2:

A second glycosylation assay of use in the invention comprises the following reporter molecules:

Tau (Wang et al., 1996, Nature Medicine, 2: 871–875; OWL accession no. P10636; Genbank accession no. X14474)

Galanthus nivalis agglutinin (Wang et al., 1996, supra; Hester et al., 1995, Nature Structural Biology, 2: 472–479; OWL accession no. P30617; Genbank accession no. M55556)

Tau from the brains of patients with Alzheimer's Disease (AD) has been shown to be glycosylated (determined by lectin binding on Western blots), whereas tau from normal brain tissue shows no sign of such glycosylation. This abnormal post-translational modification has been shown to play a role in the maintenance of the helical twists in the paired helical filament (PHF) structures formed by tau in the AD neuron (Wang et al., 1996, supra); various lectins were used in this study to identify different carbohydrate moieties on the tau protein. Galanthus nivalis agglutinin (GNA) primarily recognizes terminally-linked mannose residues. The use of this protein as an assay for the modification of Tau permits monitoring of the addition of a terminal mannose residue to a carbohydrate chain on this protein. According to certain embodiments of this assay of the invention, the addition of other residues can be monitored by substituting other lectins, with different sugar recognition specificities than that of GNA, for GNA.

The crystal structure of GNA has been determined (Hester et al., 1995, surpa), this indicates that the protein consists of a dimer of dimers with the high affinity mannose binding site formed at the interface between the A and D or, alternatively, B and C subunits. This binding site consists of strands donated from the N- and C-terminal regions of one subunit (residues 1–6 and 82–101) and also the C-terminal strand from the partner subunit (residues 102–109). It is suggested that the domain structure is indicative of a covalent link between subunits during the evolution of this tetramer (Hester et al., 1995, surpa). The assay can, therefore, be configured using the whole tetrameric assembly with a fluorescent label on only one subunit or potentially as a covalent dimer of subunits, again with one label.

An assay of this type is diagrammed as follows:

GNA-F1 + CHO-tau-F2 + mannose (GNA-F1)(mannose-CHO-tau-F2)
No FRET                                    FRET where F1 is the donor fluorophore and F2 is the acceptor. CHO represents the glycosylation of tau prior to addition of the terminal mannose.

The site for fusion of GFP to tau may be determined empirically. Labeling of the GNA subdomain on either the C- or N-terminus is equally effective.

Prenylation (Fatty Acylation)

The post-translational modification of proteins with fatty acids includes the attachment of myristic acid to the primary amino group of an N-terminal glycine residue (Johnson el al., 1994, Ann. Rev. Biochem., 63: 869–914) and the attachment of palmitic acid to cysteine residues (Milligan et al., 1995, Trends Biochem. Sci., 20: 181–186).

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (ras and MAP kinase, Itoh et al., 1993, J. Biol. Chem., 268: 3025-; ras and adenylate cyclase (in yeast; Horiuchi et al., 1992, Mol. Cell. Biol., 12: 4515) or with regulatory proteins (Shirataki et al., 1991, J. Biol. Chem., 266: 20672–20677). The prenylation status of ras is important for its oncogenic properties (Cox, 1995, Methods Enzymol., 250: 105–121) thus interference with the prenylation status of ras is considered a valuable anti-cancer strategy (Hancock, 1993, Curr. Biol., 3: 770).

Sentrinization

Sentrin is a novel 101-amino acid protein which has 18% identity and 48% similarity with human ubiquitin (Okura et al., 1996, J. Immunol., 157: 4277–4281). This protein is known by a number of other names including SUMO-1, UBL1, PIC1, GMP1 and SMT3C and is one of a number of ubiquitin-like proteins that have recently been identified. Sentrin is expressed in all tissues (as shown by Northern blot analysis), but mRNA levels are higher in the heart, skeletal muscle, testis, ovary and thymus.

The sentrinization of proteins is thought to involve the Ubiquitin-conjugating enzyme Ubc9 (Gong et al., 1997, J. Biol. Chem., 272: 28198–28201). The interaction between these two proteins in the yeast two-hybrid screen is very specific, suggesting that this is a biologically relevant phenomenon. The interaction is dependent upon the presence of the conserved C-terminal Gly-Gly residues present in sentrin (Gong et al., 1997, supra). The conjugation of sentrin to other proteins via Gly97 requires the cleavage of the C-terminal four amino acids of the protein, His-Ser-Thr-Val.

One important protein shown to be modified by the addition of sentrin is the Ran-specific GTPase-activating protein, RanGAP1, which is involved in nuclear import of proteins bearing nuclear-localization signals (Johnson and Hochstrasser, 1997, Trends Cell Biol., 7:

408–413). Conjugation of RanGAP1 and sentrin is essential both for the targeting of RanGAP1 to its binding partner on the nuclear pore complex (NPC) and for the nuclear import of proteins. Sentrin itself does not bind with high affinity to the NPC and it is, therefore, likely that it either provokes a conformational change in RanGAP1 that exposes a binding site or, alternatively, that the binding site is formed using both sentrin and RanGAP1 sequences. There is evidence to suggest that the conjugation of sentrin to RanGAP1 is necessary for the formation of other sentrinized proteins (Kamitani et al., 1997, J. Biol. Chem., 272: 14001–14004) and that the majority of these sentrinized proteins are found in the nucleus.

Sentrin has been shown in yeast two-hybrid screens to interact with a number of other proteins, including the death domains of Fas/APO1 and the TNF receptors, PML, RAD51 and RAD52 (Johnson and Hochstrasser, 1997, supra). These interactions implicate sentrin in a number of important processes. Fas/APO1 and TNF receptors are involved in transducing the apoptosis signal via their death domains. Ligation of Fas on the cell surface results in the formation of a complex via death domains and death-effector domains, triggering the induction of apoptosis. The overexpression of sentrin protects cells from both anti-Fas/APO and TNF-induced cell death (Okura et al., 1996, supra). It is not clear whether this protection is achieved simply by preventing the binding of other proteins to these death domains or whether a more complex process is involved, possibly one involving the ubiquitin pathway.

The interaction of sentrin with PML (a RING finger protein) is important, as it points to a disease state in which this protein may play a role. In normal myeloid cells, PML is found in a nuclear multiprotein complex known as a nuclear body. These nuclear bodies are disrupted in acute promyelocytic leukaemia, where a chromosomal translocation generates a fusion between regions of the retinoic acid receptor and PML. This disruption can be reversed by treatment with retinoic acid. It has been shown that PML is covalently modified at multiple sites by members of the sentrin family of proteins (but not by ubiquitin or NEDD8). Two forms of the abberent fusion protein have been identified, neither of which is modified by sentrin. It is, therefore, thought that differential sentrinization of the normal and abberant forms of PML may be important in the processes underlying acute promyelocytic leukaemia and may help in the understanding of the biological role of the PML protein (Kamitani et al., 1998, J. Biol. Chem., 273: 3117–3120).

Phosphorylation

Assay 1

SH2 domains are found in proteins involved in a number of signalling pathways and their binding to specific phosphorylated tyrosine residues is key in mediating the transmission of signals between tyrosine kinases and the proteins in the cell which respond to tyrosine phosphorylation (Waksman et al., 1993, supra and references therein). Individual SH2 domains recognize specific sequences, and the sequence specificity of a number of SH2 domains has been determined (Songyang et al., 1993, supra) using a phospho-peptide library. These data provide a number of possible domain/peptide pairs which are useful in assays of enzymatic activity according to the invention. The crystal structure of the Src SH2 domain complexed with a peptide containing its specific recognition motif from the hamster middle-T antigen (target tyrosine for phosphorylation shown in bold below) has been determined by Waksman et al. 1993 (Cell 72, 779–790).

An assay of this type may involve the following components:

v-Src SH2 domain (amino acids 148–246; Waksman et al., 1993, supra; OWL database accession no. M33292), and Hamster polyomavirus middle T antigen (Ag, below) (321–331, EPQYEEIPIYL; Waksman et al., 1993, supra; OWL database accession no. P03079).

Thus, the assay is:

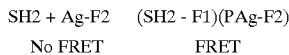

F1 is the donor fluorophore, F2 the acceptor fluorophore and P denotes the addition of a phosphate group to the target tyrosine residue.

A fluorescent protein label (e.g., Green Fluorescent Protein, GFP) is typically placed at the N-termini of both the SH2 domain and the peptide Assay 2

Phosphotyrosine binding (PTB) domains are found in a number of proteins involved in signalling pathways utilizing tyrosine phosphorylation. The PTB domain has functional similarities to the SH2 domain but differs in its mechanism of action and structure, as well as in sequence recognition (Laminet et al., 1996, J. Biol. Chem., 271: 264–269; Zhou et al., 1996, Nature Structural Biology, 3: 388–393 and references therein). These two classes of domain have little sequence identity. NMR structural analysis of the PTB domain of IRS-1 complexed with the IL-4 receptor peptide has been performed (Zhou et al., 1996, supra).

This assay involves the following components:
PTB domain of IRS-1 (amino acids 157–267) (Zhou et al., 1996, supra; OWL accession no. P35568), and Interleukin 4 Receptor (IL4R) (amino acids 489–499, LVIAGNPAYRS; Zhou et. al., 1996, supra; OWL accession no. P24394)

The assay format is as follows:

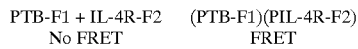

F1 is the donor fluorophore, F2 the acceptor fluorophore, and P denotes the addition of a phosphate group to the target tyrosine residue.

A fluorescent protein label (e.g., Green Fluorescent Protein, GFP) is typically placed at the N- or C-terminus of both the PTB sequence and the binding partner.

Assay 3

An assay analagous to that in assay 2 can be configured according to the invention using to the PTB domain of the proto-oncogene product Cbl and a peptide derived from the Zap-70 tyrosine kinase. The Cbl phosphotyrosine-binding domain selects a D(N/D)XpY motif and binds to the $Tyr_{292}$ negative regulatory phosphorylation site of ZAP-70 (Lupher et al., 1997, J. Biol. Chem., 272: 33140–33144).

The components of the assay are:
The Cbl N-terminal domain (amino acids 1–357; Lupher et al., 1996, J. Biol. Chem., 271: 24063–24068; OWL accession no. P22681), and Zap-70 (amino acids 284–299, $NH_3$–IDTLNSDGYTPEPARI—COOH; Lupher et al., 1996, supra; OWL accession no. P43403)

Assay 4

As stated above, Src is a member of a family of non-receptor tyrosine kinases involved in the regulation of responses to extracellular signals. Association of src with both the plasma membrane and intracellular membranes is mediated by myristoylation at the N-terminus. The enzyme has four regions which are conserved throughout the family, the SH2 domain, the SH3 domain, the kinase or SH1 domain and the C-terminal tail. In addition there is a unique region which does not have homology between family members (Brown and Cooper, 1996, Biochim. Biophys. Acta, 1287: 121–149).

The SH2 domain binds tightly to specific tyrosine phosphorylated sequences. This affinity plays a role in the interaction between src and other cellular proteins and also in the regulation of the kinase by phosphorylation. The C-tenninal tail of src can be phosphorylated on $Tyr_{530}$, which phosphorylation leads to almost complete inhibition of kinase activity. There is strong evidence that this inhibition is achieved by the interaction of the C-terminal tail with the SH2 domain. This interaction is thought to promote a conformational change to the 'closed' conformation which is further stabilized by the participation of the SH3 and kinase domains in intramolecular contacts.

This assay involves the following component.
c-Src (residues 86–536; Xu et al., 1997, Nature, 385: 595–602; GenBank Accession No. K03218).

The assay is diagrammed as follows:

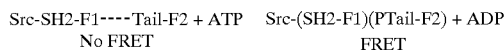

where F1 is the donor fluorophore, F2 is the acceptor fluorophore and P denotes. the addition of a phosphate group to the target tyrosine residue.

When a fluorescent protein is used in an assay such as this, using an intramolecular interaction to follow chemical modification, it is appropriate to place GFP between domains using a flexible linker to preserve protein domain interactions. This allows the GFP variants to approach more closely and increase the efficiency of the FRET achieved, but must be balanced by the need to achieve a good distance between variants in the 'No FRET' state. If sufficient spacing between donor and acceptor fluorophores or, alternatively, between a fluorophore or other label and a quencher therefor, is not achieved in this manner, other candidate locations for fluorescent protein fusion include, but are not limited to, the C-terminus and the region between the SH2 domain and the SH2-kinase linker.

Proteases

As noted above, susceptibility to modification includes the possibility that the polypeptide may be subjected to proteolytic degradation under the appropriate conditions, which in a preferred embodiment means that the polypeptide is cleaved by a protease at a recognition site for the protease enzyme. Alternatively, however, the polypeptide may be susceptible to digestion by an exoprotease, from the N or C terminus.

Where engineered polypeptides are used, they should be constructed such that the protease cleavable site is positioned such that cleavage thereof disrupts binding of the polypeptide in the context of the multimer. Thus, polypeptides which have been subjected to protease cleavage should dissociate from the multimer. Preferably, the protease does not cleave the polypeptide in such a manner that the label becomes detached therefrom without the binding abilities thereof being disrupted. Location of the protease cleavable site may be determined empirically. As a guide, however, the site should be placed within or proximal to the binding domain which is responsible for the multimerisation of the polypeptide.

In the case of coiled coil binding domains, Lumb et al (Subdomain folding of the coiled coil leucine zipper from the bZIP transcriptional activator GCN4, Lumb, K. J., Carr, C. M. & Kim, P. S., Biochemistry (1994) 33 7361–7367) teach that the loss of ten residues from the N-terminus or seven from the N- and six from the C-terminus is sufficient to destabilise the coiled coil peptide sequence known as GCN4-p1 (Evidence that the leucine zipper is a coiled coil, O'Shea, E. K., Rutkiowski, R. & Kim, P. S. (1989) Science 243 538–542). Su et al provide data indicating that there is a sharp decrease in the stability of a designed coiled coil with a decrease in chain length from 23 to 19 residues (Su, J. Y., Hodges, R. S. & Kay, C. M., Biochemistry (1994)33 15501–15510). Accordingly, cleavage sites may positioned such that the coiled coil is disrupted to an extent that it is no longer capable of directing multimerisation.

A number of proteases and their cleavage sites are known in the art, and set forth in Table 4

TABLE 4

| Protease | Cut Site(s) | Possible/Proven Role |
|---|---|---|
| Aminopeptidase M | Hydrolysis from free N-terminus | digestion |
| Carboxypeptidase Y | Hydrolysis from C-terminus | digestion |
| Caspase 1, 4, 5 | W/LEHD-X[#] | mediator of apoptosis |
| Caspase 2, 3, 7 | DEXD-X[#] | mediator of apoptosis |
| Caspase 6, 8, 9 | L/VEXD-X[#] | mediator of apoptosis |
| Chymotrypsin | Y-X, F-X, T-X, (L-X, M-X, A-X, E-X) | digestion |
| Factor Xa | IEGR-X | blood clotting cascade |
| Pepsin | F-Z, M-Z, L-Z, W-Z (where Z is a hydrophobic residue) but will cleave others | digestion |
| TEV | E (N) XYXQ-S/G[−] | polyprotein processing/as a reagent |
| Thrombin | R-X | blood clotting cascade |
| Trypsin | R-X, K-X | digestion |

[#]Ideal cut sites identified by Thornberry et al in A combinatorial approach defines specificities of members of the caspase family and granzyme B, Journal of Biological Chemistry 272 17907–17911.
[−]Release of proteins and peptides from fusion proteins using a recombinant plant virus proteinase, Parks, T. D., Keuther, K. K., Howard, E. D., Johnston, S. A. & Dougherty, W. G., Analytical Biochemistry (1994) 216 413–417; Life Technologies Ltd.

The foregoing, or other, sites may be engineered into or close to the binding domains of polypeptides used in the methods of the invention.

In a preferred aspect of the present invention, it is desirable to engineer specificity into the polypeptide, such that it is digested only by the desired protease and only at the intended protease cleavable site. This may be achieved, for example, by the use of D-isomers of amino acids in the construction of the polypeptide. D-amino acids are resistant to protease digestion, and a polypeptide constructed of D-amino acids will withstand proteolytic attack. Moreover, use of D-amino acids does not interfere with the protein-protein interactions involved in multimerisation, such as the interaction of protein binding domains, especially coiled-coil domains, provided that D amino acids are employed in both members of a binding pair.

In order to allow digestion by the intended protease enzyme, the D-amino acid constructions of the polypeptides of the invention contain one or more parts constructed of L-amino acids, or otherwise rendered susceptible to proteolytic digestion. For example, coiled coils constructed of D-amino acids preferably comprise inserts, constructed wholly or partly of L-amino acids, which contain the protease cleavage site. The L-amino acid insert may be of any size, and may be positioned between coiled coil repeats, or between residues of the coiled coil. Preferred are insertions at positions b-c, e-f and f-g. The insert is covalently attached to the coiled coil, through a covalent linkage to the backbone or through a sidechain.

The insert may comprise only a cleavage site, or an entire polypeptide. Functionally, the insert is sufficiently flexible to permit the coiled coil to bind to its target efficiently when the insert is intact. For example, the insert may comprise a flexible linker, such as a gly-gly linker. Molecules comprising D-amino acids are advantageously employed in in vitro assays.

Inserts as described above may be employed in D-amino acid coiled coils, in conventional L-amino acid coiled coils, or in coiled coils which are partially D and partially L in construction. For example, a coiled coil may be constructed such that it consist of L-amino acids on one side of the insert, and D-amino acids on the other side thereof.

G. Assays for in vivo Detection Enzymes via their Effect on Protein-Protein Interactions According to the invention, methods are provided for measuring enzyme activity via an effect on interactions between a binding domain and a binding partner thereof in vivo. Specifically, transgenic multicellular organisms may be produced that express in the same cell both the binding domain and binding partner. The binding of the binding domain and the binding partner to one another may be determined by means of a detectable label on at least one of the polypeptides, typically both. The physical characteristics of the labels alter in a measurable way depending on the molecular environment in which the polypeptides are found. Thus, in particular, the physical characteristics of the labels will alter depending on whether the binding domain and binding partner are bound to one another. Measurement of the physical characteristics of the labels will allow a determination of the extent of binding. The use of non-invasive measuring techniques will make it possible to follow the interactions over time in living cells, such as in situ in an intact multicellular organism and/or in a biological sample taken from a multicellular organism. The results obtained may be used to obtain physiologically relevant information such as kinetic and/or spatial information about the nature of the interaction between the binding domain and binding partner.

Clearly, in an in vivo situation, binding will be influenced by a number of factors such as polypeptide competitors and stimuli acting on signal transduction pathways leading to, for example, post-translational modifications, notably phosphorylation. Thus, an important application of the method of the invention is to study the effect on the binding of the binding domain to the binding partner of substances that stimulate cells within a transgenic organism of the invention, such as receptor agonists and antagonists.

For example, a compound may be known to have an inhibitory effect on the activity of a protein kinase in vitro. The protein kinase is typically known to phosphorylate and promote the binding of a binding domain to a binding partner. Thus, if the compound is administered to a transgenic animal that expresses the binding domain and binding partner, labeled with a detectable label, then the consequential effect on the association of the binding domain and binding partner may be assessed in situ, in particular in a range of different tissues to determine if the effect is confined to particular cell types.

The assay system may be used in an intact, living multicellular organism, such as an insect or a mammal. Methods of generating transgenic Drosophila, mice and other organisms, both transiently and stably, are well known in the art (see above); detection of fluorescence resulting from the expression of Green Fluorescent Protein in live Drosophila is well known in the art. Where the expression of the nucleotide constructs is under the control of a inducer, sufficient time is allowed to pass after administration of the inducer molecule to allow for gene expression, for binding of a binding domain to its binding partner and for chromophore maturation, if necessary (e.g., Green Fluorescent Protein matures over a period of approximately 2 hours prior to fluorescence) before fluorescence or other emission from a detectable label is measured. A reaction component (particularly a candidate modulator of enzyme function) which is not administered as a nucleic acid molecule may be delivered by a method selected from those described below.

In vivo assays may be carried out in situ or using one or more cells removed from the transgenic organism. The one or more cells may be obtained from any subset of the tissues of the organism. Methods for visualising bioluminescence in living mammals are described in Contag et al., 1997, Photochemistry and Photobiology 66: 523–531 reviewed in Contag et al., 1998, Nature Medicine 4: 245–247 (see also references therein).

Alternatively, or in addition, in vitro assays of interactions between the binding domain and binding partner may be performed using extracts from a biological sample comprising one or more cells taken from a transgenic animal of the invention or body fluids, whether to test the activity of a recombinant protein or one which is found in nature. The use of a crude cell extracts and/or body fluids enables rapid screening of many samples, which potentially finds special application in high-throughput screening methods, e.g. of candidate modulators of the binding domain-binding partner interaction. However, it is generally intended that in vitro assays are to be used as a precursor to, or for confirmation of, the in vivo assays of the invention.

As used herein, the term "biological sample" refers to a subset of the tissues of a biological organisms, its cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" and "biological specimen" further refer to a homogenate, lysate or extract prepared from a whole organism or a subset of its tissues, cells or component parts, or a fraction or portion thereof.

Candidate Modulators of Protein-Modifying Enzymes to be Screened According to the Invention The present invention encompasses methods by which to screen compositions which may enhance, inhibit or not affect (e.g., in a cross-screening procedure in which the goal is to determine whether an agent intended for one purpose additionally affects general cellular functions, of which protein modification is an example) the interaction of a binding domain and binding partner in vivo, in particular as modulated by the activity of a protein-modifying enzyme.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 500 daltons. Exemplary classes include heterocycles, peptides, saccharides, steroids, and the like The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target mRNA. Ribozymes of the hammerhead class are the smallest known, and tend themselves both to in vitro production and delivery to cells.

Determination of Activity of Candidate Modulator of a Protein-Protein Interaction or Protein-Modifying Enzyme A candidate modulator of the interaction between a binding domain and a binding partner assayed according to the invention as described herein, is determined to be effective if its use results in a difference of about 10% or greater relative to controls in which it is not present (see below) in FRET or other signal emanating from a detectable label of use in the invention resulting from the association of a natural binding domain with its binding partner.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where $\text{Index}_{Control}$ is the quantitative result (e.g., amount of or rate of change in fluorescence at a given frequency, rate of molecular rotation, FRET, rate of change in FRET or other index of modification, including, but not limited to, enzyme inhibition or activation) obtained in assays that lack the candidate modulator (in other words, untreated controls), and $\text{Index}_{Sample}$ represents the result of the same measurement in assays containing the candidate modulator. As described herein, control measurements are made with a differentially-labeled natural binding domain and its corresponding partner only and with these molecules plus a protein-modifying enzyme which recognizes a natural site for post-translational protein modification present on the binding domain and, optionally, on the binding partner.

Such a calculation is used in either in vitro or in vivo assays performed according to the invention.

Dosage and Administration of a Candidate Modulator thereof for use in an in vivo Assay of the Invention Dosage The amount of a candidate modulator will typically be in the range of about 1 µg to 100 mg/kg body weight. Where the candidate modulator is a peptide or polypeptide, it is typically administered in the range of about 100 to 500 µg/ml per dose. A single dose of a candidate modulator, or multiple doses of such a substance, daily, weekly, or intermittently, is contemplated according to the invention.

A candidate modulator is tested in a concentration range that depends upon the molecular weight of the molecule and the type of assay. For example, for inhibition of protein/protein or protein/DNA complex formation or transcription initiation (depending upon the level at which the candidate modulator is thought or intended to modulate the activity of a protein modifying enzyme according to the invention), small molecules (as defined above) may be tested in a concentration range of 1 pg to 100 µg/ml, preferably at about 100 pg to 10 ng/ml; large molecules, e.g., peptides, may be tested in the range of 10 ng to 100 µg/ml, preferably 100 ng to 10 µg/ml.

Administration

Generally, nucleic acid molecules are administered in a manner compatible with the dosage formulation, and in such amount as will be effective. The amount of a nucleic acid encoding a candidate modulator must be sufficient to ensure production of an amount of the candidate modulator which can, if effective, produce a change of at least 10% in the effect of the target on FRET or other label emission resulting from binding of a binding domain to its binding partner or, if administered to a patient, an amount which is prophylactically and/or therapeutically effective.

When the end product (e.g. an antisense RNA molecule or ribozyme) is administered directly, the dosage to be administered is directly proportional to the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5 to 1 µg, or 1 to 10 µg, or optionally 10 to 100 µg of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

If no effect (e.g., of a protein modifying enzyme or an inhibitor thereof) is seen within four orders of magnitude in either direction of the starting dosage, it is likely that a protein modifying enzyme does not recognize the target site of the binding domain (and, optionally, its binding partner) according to the invention, or that the candidate modulator thereof is not of use according to the invention. It is critical to note that when high dosages are used, the concentration must be kept below harmful levels, which may be known if an enzyme or candidate modulator is a drug that is approved for clinical use. Such a dosage should be one (or, preferably, two or more) orders of magnitude below the $LD_{50}$ value that is known for a laboratory mammal, and preferably below concentrations that are documented as producing serious, if non-lethal, side effects.

Components of screening assays of the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

Administration of a candidate modulator as described herein may be either localized or systemic.

Localized Administration

Localized administration of a component of an assay of the invention is preferably by via injection or by means of a drip device, drug pump or drug-saturated solid matrix from which the candidate modulator therefor or nucleic acid encoding the same can diffuse implanted at the target site. When a tissue that is the target of delivery according to the invention is on a surface of an organism, topical administration of a pharmaceutical composition is possible.

Compositions comprising a composition of, or of use in the invention which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a candidate modulator is to be delivered for assay (or, if found effective, for therapeutic use) is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, J. Clin. Invest., 84: 1349–1354).

Systemic Administration

Systemic administration of a protein, nucleic acid or other agent according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced protein, nucleic acid or other material or may, instead, comprise cells that produce and secrete a natural binding domain and/or a binding partner therefor, protein modifying enzyme or candidate modulator thereof. Note that injection may be performed either by conventional means (i.e. using a hypodermic needle) or by hypospray (see Clarke and Woodland, 1975, Rheumatol. Rehabil., 14: 47–49). Components of assays of the invention can be given in a single- or multiple dose.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

H. Uses

The invention is useful in monitoring the activity of a protein-modifying enzyme present in a living cell, in particular the cells of a multicellular organism. The invention is further useful in assaying a cell or cell extract for the presence- or level of activity of a protein modifying enzyme. The invention is additionally useful in assaying the activity of naturally-occurring (mutant) or non-natural (engineered) isoforms of known protein modifying enzymes or, instead, that of novel (natural or non-natural) enzymes. The invention is of use in assaying in vivo the efficacy of candidate modulators of a protein-protein interaction and/or the activity of a protein modifying enzyme in inhibiting or enhancing the activity of that enzyme; moreover, is useful to screen potential therapeutic drugs for activity against cloned and/or purified enzymes that may have important clinical pathogenicities when mutated. The invention is further of use in the screening of candidate bioactive agents (e.g., drugs) for side effects, whereby the ability of such an agent to modulate a protein-protein interaction and/or the activity of a protein modifying enzyme may be indicative a propensity toward provoking unintended side-effects to a therapeutic or other regimen in which that agent might be employed.

Particular areas of interest include the treatment of immune-related disorders such as organ transplant rejection and autoimmune diseases The spectrum of autoimmune disorders ranges from organ specific diseases (such as thyroiditis, insulitis, multiple sclerosis, iridocyclitis, uveitis, orchitis, hepatitis, Addison's disease, myasthenia gravis) to systemic illnesses such as rheumatoid arthritis or lupus erythematosus. Other disorders include immune hyperreactivity, such as allergic reactions, in particular reaction associated with histamine production, and asthma.

The present invention will now be illustrated by means of the following examples which are illustrative only and not limiting.

DESCRIPTION OF THE FIGURES

FIG. 1 is a graph showing FRET ratios over time in the presence or absence of PKA and/or a PKA inhibitor The X-axis shows time in minutes, while the Y-axis shows the FRET ratio. Filled squares: no PKA; filled triangles: with PKA and with PK1 (PKA inhibitor); filled diamonds: with PKA. Time of addition is marked with downward pointing arrow.

EXAMPLES

Example 1

Measurement of the Interaction Between ZAP70 and TCRζ in vivo.

Engagement of the T cell receptor (TCR) by an antigen/major histocompatibility complex (MHC) results in T cell activation. After antigen stimulation, the ζ chain of the TCR is phosphorylated by the src family tyrosine kinases Lck and Fyn. This phosphorylation occurs on specific tyrosine residues present in immunoreceptor tyrosine-based activated motifs (ITAMs). The SH2 domain of another tyrosine kinase, ZAP70, binds to phosphorylated TCRζ thereby activating ZAP70 and continuing the transmission of the T cell activation response signalling cascade. Thus the TCRζ ITAM and the SH2 domain of ZAP70 represent domains that are dependent on phosphorylation for an interaction to occur and may be used in the assay methods of the invention as an indicator of Lck and Fyn kinase activity in response to T cell activation.

Constructs pZAP70-GFP comprises the ZAP70 SH2 domain coding sequence (Gauen et al., 1994, Mol. Cell. Biol. 14: 3729–3741—Accession no. P43404—gi:1177045) fused upstream of the GFP coding sequence (Stauber et al., 1998, Biotechniques 24: 462–471 and references therein) and under the control of a 2.0 kb fragment of the T cell-specific CD2 LCR (Lang et al., 1991, Nucl. Acids Res. 19: 5851–5856; Drabek et al., 1997, Gene Ther. 4: 93–100).

pTCRz-BFP comprises the TCRζ domain coding sequence (Baniyash et al., 1989, J. Biol. Chem. 264(22), 13252–13257—Accession no. AAA50301.1) fused downstream of the BFP coding sequence (Stauber et al., 1998, supra and references therein) and under the control of a 2.0 kb fragment of the T cell-specific CD2 LCR (Lang et al., 1991, supra; Drabek et al., 1997, supra).

Construction of Transgenic Mice

Mouse oocytes are injected with pZAP70-GFP and pTCRz-BFP as described in Drabek et al., 1997, supra. Injected eggs are transferred into pseudopregnant mice and transgenic offspring identified by Southern blot or PCR analysis of tail DNA for GFP and BFP sequences. Germline tissue is also analysed by Southern blot or PCR analysis.

Analysis of T Cells for Protein Expression

T cells are purified from blood, lymph nodes or thymus tissue of transgenic animals by positive selection on magnetic CD4-antibody-coated beads specific for particular cell types (MACS columns) according to the manufacturer's instructions (Miltenyi Biotech) which are as follows:

Lymph nodes or thymus tissue are removed and single cell suspensions prepared in tissue culture medium ($10^8$ cells in 0.4 ml RPMI 1640 with 10% FCS). Cells are incubated at 4° C. for 15 mins, passed over the MACS separation column, washed and collected. CD4-positive cells may be enriched by negative selection on anti-CD8 antibody-coated magnetic beads.

Cell extracts are prepared by boiling in SDS-PAGE running buffer and resolved by SDS-PAGE followed by western blotting and detection of proteins using suitable antibodies. The results show measurable expression of both ZAP70-GFP and TCRζ-BFP in transgenic animals.

Analysis of ZAP70-TCRζ Interactions in T Cells Using FRET

T cells prepared as described above are pelleted and resuspended in ice cold PBS pH 7.4. Cells are washed in PBS/1% BSA and aliquoted at $10^6$ cells per well into a microtitre plate. Cells are left unstimulated at 37oC. for 10 mins and then stimulated using an anti-CD3 antibody (control cells are not stimulated or incubated with a control antibody). Fluorescence is measured using a FACS machine over a time course of about 30 minutes.

Example 2

Measurement of the Interaction Between Syk and the IgE Receptor in vivo

Activated mast cells secrete histamine which is responsible for the sneezing and itching symptoms associated with allergic reactions. When IgE binds to the IgE receptor on the surface of mast cells this activates the tyrosine kinase Lyn which then phosphorylates the γ subunit of the receptor. A second kinase, Syk, binds to the phosphorylated γ subunit and becomes activated, phosphorylating a wide range of downstream signaling molecules that eventually result in histamine secretion. Thus the IgE receptor γ subunit and the SH2 domain of Syk represent natural binding domains that are dependent on phosphorylation for an interaction to occur and may be used in the assay methods of the invention as an indicator of Lyn kinase activity.

Constructs pIgEγ-GFP comprises the IgE receptor y subunit coding sequence (Ra et al., 1989, J. Biol. Chem. 264: 15323–15327; Accession No. J05020.1) fused upstream of the GFP coding sequence (Staubder et al., 1998, supra and references therein) and under the control of a 2.0 kb fragment of the T cell-specific CD2 LCR (Lang et al., 1991. supra; Drabek et al., 1997, supra).

pSykSH2-BFP comprises the Syk kinase SH2 domain coding sequence (Fluck et al., 1995, Biochem. Biophys. Res. Commun. 213: 273–281; Accession No. Z49877.1) fused downstream of the BFP coding sequence (Stauber et al., 1998, supra and references therein) and under the control of a 2.0 kb fragment of the T cell-specific CD2 LCR (Lang et al., 1991, supra; Drabek et al., 1997, supra).

Construction of Transgenic Mice

Mouse oocytes are injected with pIgEγ-GFP and pSykSH2-BFP as described in Drabek et al., 1997, supra. Injected eggs are transferred into pseudopregnant mice and transgenic offspring identified by Southern blot or PCR analysis of tail DNA for GFP and BFP sequences. Germline tissue is also analysed by Southern blot or PCR analysis.

Analysis of IgE-Syk Interactions in Mouse Tissue Using FRET

Biopsies of mouse lymph tissue are washed in ice-cold PBS/1% BSA and aliquots transferred into microtitre plate wells. Plates are incubated at 37° C. in the presence or absence of IgE. Fluorescence is measured using a FACS machine over a time course of about 30 minutes.

Example 3

Determination of the Activity of Protein Kinase A Using Peptidic Pesudosubstrates DNA encoding basic and acidic hetero-dimeric coiled-coils (similar to those described in O'Shea et al., 1993, Cur. Biology 3: 658–667) was inserted between the BamHI and EcoRI sites of the Quantum GFP and BFP vectors QBI25fC1 and QBI50fC1, respectively. The original coiled-coil molecules were modified each to contain a PKA phosphorylation site in the middle (underlined) of the coiled-coils.

| Coiled coil | |
|---|---|
| | DNA Sequence |
| 4HAphos | GGATCCTCTACAAGGGTATTGCTCAGTTGGAGCAGGAAATCC GCCGCCTTCGCCGCAAAAGCGCACAACTTGAACAAGAGATCG CTCAGCTTGAGCAGGAAAAGCTTTAAGAATTC |
| 5HBphos | GGATCCTCTATAAAGGCATCTGTCAGCTTCGCCAACGCATCC GCCGCCTTCGCCGCAAAAGCGCTCAACTCCGCCAACGCATTG CCCAGCTCCGCCAGCGCATTGCCCAGCTCCGCCAGCGCAAGC TTTAAGAATTC |
| | Protein Sequence |
| 4HAphos | YRILYKGIAQLEQEIRRLRRKSAQLEQEIAQLEQE |
| 5HBphos | YRILYKGICQLRQRIRRLRRKSAQLRQRIAQLRQRIA QLRQR |

Experiments were performed to confirm that FRET occurred between the two constructs. FRET was detected at an equivalent level (~10-fold) to the constructs not containing the phosphorylation sites (data not shown). The FRET experiments were then performed in the presence of PKA. As can be seen from FIG. 1, the addition of PKA disrupts the FRET between the phosphorylation constructs. The effect of PKA on FRET can be blocked by the addition of PKI a specific inhibitor of the kinase. These results demonstrate the feasibility of the use of proteinaceous fluorophores for protein kinase assay.

Example 4

Determination of the Activity of Protein Kinase A Using Peptidic Pesudosubstrates in Transgenic Animals Two vectors, one encoding the 4HAphos sequence fused to BFP and the other encoding the 5HBphos sequence fused to GFP, under the control of a β-actin promoter are constructed and introduced into different fertilised mouse oocytes and transgenic mice produced as described in Ikawa et al., 1995, FEBS Lets. 375:125–128 and Okabe et al., 1997, FEBS Lets. 407: 313–319. The resulting transgenic mice are mated to produce transgenic mice expressing both coding sequences. The expression of the fluorescent proteins is examined in pups illuminated with UV light.

Tissue samples, such as spleen, are extracted from animals killed at the age of 4–6 weeks. The samples are then preincubated with forskolin (about 100 μM) or 8-CPTcAMP (1.5 mM) for about 30 mins to activate PKA and the cells examined using FRET to is confirm that PKA activation has occurred. The cells are then incubated with a PKA inhibitor (PKI) for between 5 and 100 mins and the cells examined using FRET to determine the extent of PKA inhibition.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by the following numbered paragraphs:

1. A method of measuring in vivo in a transgenic non-human multicellular organism the activity of a cellular enzyme, which organism is transgenic by virtue of comprising one or more nucleic acid constructs encoding a binding domain and a binding partner thereof, wherein:
   (i) the binding domain and/or binding partner comprise a site subject to post-translational modification by the cellular enzyme;
   (ii) modification of the site by the enzyme affects the interaction between the binding domain and binding partner; and
   (ii) the binding domain and binding partner each comprise a detectable label such that when the binding domain and binding partner interact, a detectable physical characteristic of one or both of the labels is altered,
which method comprises measuring the interaction between the binding domain and the binding partner by measuring changes in said physical characteristic in one or more cells of the transgenic organism.

2. A method according to paragraph 1 wherein the binding domain and binding partner are present as separate nucleic acid constructs stably present in the germline of the transgenic organism.

3. A method according to paragraph 1 or 2, wherein said physical characteristic is light emission/absorption.

4. A method according to paragraph 3, wherein said physical characteristic is fluorescent light emission.

5. A method according to paragraph 4 wherein the detectable label is a fluorescent protein.

6. A method according to paragraph 4 or 5, wherein said method further comprises exciting said detectable label and monitoring fluorescence emission.

7. A method according to any one of the preceding paragraphs, wherein said enzyme is selected from a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, an NAD:Arginine ADP ribosyltransferase, a protease, a protein kinase and a protein phosphatase.

8. A method according to paragraph 6 or 7 wherein said method further comprises the step, prior to, during or after measurement of the physical characteristic, of contacting said binding domain and said binding partner with a compound which modulates the activity of said enzyme.

9. A method of identifying a compound capable of modulating the activity of a cellular enzyme which method comprises
   (i) contacting one or more cells of a transgenic non-human multicellular organism as defined in paragraph 1 with a candidate substance
   (ii) measuring the activity of the enzyme in said cells by the method of paragraph 1; and
   (iii) determining whether the activity of the enzyme is affected.

10. A transgenic non-human multicellular organism, which organism is transgenic by virtue of comprising one or more nucleic acid constructs encoding a binding domain and a binding partner, which constructs are stably present in the germline of the transgenic organism, wherein
    (i) the binding domain and/or binding partner comprise a site subject to post-translational modification by a cellular enzyme;
    (ii) modification of the site by the enzyme affects the interaction between the binding domain and binding partner; and
    (ii) the binding domain and binding partner each comprise a detectable label such that when the binding domain and binding partner interact, a detectable physical characteristic of one or both of the labels is altered.

11. A transgenic organism according to paragraph 10 wherein the binding domain and binding partner are present as separate nucleic acid constructs stably present in the germline of the transgenic organism.

12. A transgenic organism according to paragraph 10 or 11, wherein said physical characteristic is light emission/absorption.

13. A method according to paragraph 12, wherein said physical characteristic is fluorescent light emission.

14. An organism according to paragraph 13 wherein the detectable label is a fluorescent protein.

15. An organism according to any one of paragraphs 10 to 14, wherein said enzyme is selected from a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, an NAD:Arginine ADP ribosyltransferase, a protease, a protein kinase and a protein phosphatase.

16. An organism according to any one of paragraphs 10 to 15 wherein said organism is an animal.

17. An organism according to any one of paragraphs 10 to 15 wherein said organism is a plant.

18. An organism according to any one of paragraphs 10 to 17 said nucleic acid constructs comprise a locus control region.

19. A method of producing a transgenic organism as defined in any one of paragraphs 10 to 18 which method comprises crossing a first transgenic organism comprising a nucleic acid construct encoding a binding domain comprising a detectable label, which construct is stably present in the germline of the first transgenic organism, with a second transgenic organism comprising a nucleic acid construct encoding a binding partner comprising a detectable label, which construct is stably present in the germline of the second transgenic organism.

20. A transgenic organism obtainable by the method of paragraph 19.

21. A compound capable of modulating the activity of a cellular enzyme which compound is identified by the method of paragraph 9.

22. A compound according to paragraph 21 for use in therapy.

What is claimed is:

1. A method of measuring an activity of a cellular protein-modifying enzyme comprising:
   obtaining a transgenic nonhuman organism whose genome comprises one or more nucleic acid constructs comprising a transgene encoding a fusion protein comprising a binding domain fused to a first detectable label and a transgene encoding a fusion protein comprising a binding partner of the binding domain fused to a second detectable label operably linked to a promoter, wherein expression of the transgenes result in production of the fusion proteins; and detecting the interaction between the binding domain and the binding partner of said fusion proteins by measuring changes in a physical characteristic of said labels in one or more cells of the transgenic organism; wherein (i) the binding domain and/or binding partner comprise a site subject to post-translational modification by a cellular protein-modifying enzyme;

(ii) modification of the site by the enzyme affects the interaction between the binding domain and binding partner; and (iii) the detectable labels fused to the binding domain and binding partner are such that when the binding domain and binding partner interact, a change in said physical characteristic is detected by measuring an alteration of one or both of the labels.

2. The method according to claim 1 wherein the binding domain and the binding partner are encoded by separate nucleic acid constructs.

3. A method according to claim 1, wherein said physical characteristic is light emission/absorption.

4. A method according to claim 3, wherein said physical characteristic is fluorescent light emission.

5. A method according to claim 4 wherein the detectable label is a fluorescent protein.

6. A method according to claim 4, wherein said method further comprises exciting said detectable label and monitoring fluorescence emission.

7. A method according to claim 1, wherein said enzyme is selected from a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, an NAD:Arginine ADP ribosyltransferase, a protease, a protein kinase and a protein phosphatase.

8. A method according to claim 7 wherein said method further comprises the step, prior to, during or after measurement of the physical characteristic, of contacting said binding domain and said binding partner with a compound which modulates the activity of said enzyme.

9. A transgenic nonhuman organism whose genome comprises one or more nucleic acid constructs comprising a transgene encoding a fusion protein comprising a binding domain fused to a first detectable label and a transgene encoding a fusion protein comprising a binding partner of the binding domain fused to a second detectable label operably linked to a promoter, wherein expression of the transgene results in production of the fusion proteins; wherein (i) the binding domain and/or binding partner comprise a site subject to post-translational modification by a cellular protein-modifying enzyme;

(ii) modification of the site by the enzyme affects the interaction between the binding domain and binding partner; and (iii) the detectable labels fused to the binding domain and binding partner are such that when the binding domain and binding partner interact, a change in said physical characteristic is detected by measuring an alteration of one or both of the labels.

10. A transgenic organism according to claim 9 wherein the binding domain and the binding partner are encoded by separate nucleic acid constructs.

11. A transgenic organism according to claim 9, wherein said physical characteristic is light emission/absorption.

12. A method according to claim 11, wherein said physical characteristic is fluorescent light emission.

13. An organism according to claim 12 wherein the detectable label is a fluorescent protein.

14. An organism according to any one of claim 9, wherein said enzyme is selected from a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, an NAD:Arginine ADP ribosyltransferase, a protease, a protein kinase and a protein phosphatase.

15. An organism according to any one of claim 9 wherein said organism is an animal.

16. An organism according to any one of claim 9 wherein said organism is a plant.

17. An organism according to any one of claim 9 wherein said nucleic acid constructs comprise a locus control region.

18. A method of producing a transgenic organism as defined in claim 10 which method comprises mating a first transgenic organism whose genome comprises a nucleic acid construct comprising a transgene encoding a fusion protein comprising a binding domain and a first detectable label operably linked to a promoter with a second transgenic organism whose genome comprises a nucleic acid construct comprising a transgene encoding a fusion protein comprising a binding partner of the binding domain and a second detectable label operably linked to a promoter, wherein expression of the transgenes results in production of said fusion proteins.

19. A transgenic organism made by the method of claim 18 wherein the genome of said transgenic organism comprises a nucleic acid construct comprising a transgene encoding a fusion protein comprising a binding domain and a first detectable label operably linked to a promoter and a nucleic acid construct comprising a transgene encoding a fusion protein comprising a binding partner of the binding domain and a second detectable label operably linked to a promoter, wherein expression of the transgenes results in production of said fusion proteins; wherein (i) the binding domain and/or binding partner comprise a site subject to post-translational modification by a cellular protein-modifying enzyme;

(ii) modification of the site by the enzyme affects the interaction between the binding domain and binding partner; and (iii) the detectable labels fused to the binding domain and binding partner are such that when the binding domain and binding partner interact, a change in said physical characteristic is detected by measuring an alteration of one or both of the labels.

* * * * *